(12) United States Patent
Yang et al.

(10) Patent No.: US 7,459,460 B2
(45) Date of Patent: Dec. 2, 2008

(54) TRISUBSTITUTED HETEROAROMATIC COMPOUNDS AS CALCIUM SENSING RECEPTOR MODULATORS

(75) Inventors: Wu Yang, Princeton Junction, NJ (US); John K. Dickson, Apex, NC (US); Christopher B. Cooper, Lawrenceville, NJ (US); Dharmpal S. Dodd, Princeton, NJ (US); Zheming Ruan, Dayton, NJ (US); Dora M. Schnur, Hamilton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 517 days.

(21) Appl. No.: 10/854,484

(22) Filed: May 26, 2004

(65) Prior Publication Data

US 2005/0004151 A1    Jan. 6, 2005

Related U.S. Application Data

(60) Provisional application No. 60/473,904, filed on May 28, 2003.

(51) Int. Cl.
| | | |
|---|---|---|
| C07D 213/36 | (2006.01) | |
| C07D 239/42 | (2006.01) | |
| C07D 401/04 | (2006.01) | |
| C07D 403/04 | (2006.01) | |
| A61K 31/4418 | (2006.01) | |
| A61K 31/444 | (2006.01) | |
| A61K 31/505 | (2006.01) | |
| A61K 31/506 | (2006.01) | |

(52) U.S. Cl. .................. 514/275; 544/330; 544/331
(58) Field of Classification Search ............... 544/330, 544/331; 514/275
See application file for complete search history.

(56) References Cited

U.S. PATENT DOCUMENTS

| 4,411,890 A | 10/1983 | Momany |
| 6,432,963 B1 | 8/2002 | Hisamichi et al. |

FOREIGN PATENT DOCUMENTS

| EP | 360701 | * | 3/1990 |
| WO | WO 89/07110 | | 8/1989 |
| WO | WO 89/07111 | | 8/1989 |
| WO | WO 93/04081 | | 3/1993 |
| WO | WO 00/43279 | * | 12/2000 |
| WO | WO 02/066036 | * | 8/2002 |

OTHER PUBLICATIONS

Pepin et al., CAPLUS Abstract 113:78409, 1990.*
Beers et al., Gastrointestinal Disorders, The Merck Manual of Diagnosis and Therapy, Seventeenth Edition (online), Section 3, Chapter 31, 1999.*
Bremner et al., Therapy of Crohn's Disease in childhood, Expert Opin. Pharmacother. 3(7), pp 809-825, 2002.*
Singh et al., Immune Therapy in inflammatory bowel disease and models of colitis, British Journal of Surgery, 88, pp. 1558-1569, 2001.*
Robinson, Medical Therapy of Inflammatory Bowel Disease for the 21st Century, Eur. J. Surg. 164, Suppl. 582, pp. 90-98, 1998.*
Hebert et al., Functions and roles of the extracellular Ca2+ -sensing receptor in the gastrointestinal tract, Cell Calcium 35, pp. 239-247, 2004.*
Putney, Jr. et al., Mechanisms of capacitative calcium entry, Journal of Cell Sciences 114(12), pp. 2223-2229, 2001.*
Bundgaard, Design of Prodrugs: Introduction, p. 1, 1985.*
Silverman, Prodrugs and Drug Delivery Systems, The Organic Chemistry of Drug Design and Drug Action, pp. 352-400, 1992.*
Arndt, D., "Mangan-Verbindungen als Oxidationsmittel in der organischen Chemie", Methoden der Organischen Chemie (Houben-Weyl), Fourth Edition, vol. 4, Part 1b, Georg Thieme Verlag, Stuttgart, publ., Müller, Ed., ed., pp. 466-672 (1975).
Betts, M.J. et al., " 'Hidden' axial chirality as a stereodirecting element in reactions involving enol(ate) intermediates. Part 2. Cyclisation reactions of methyl (4R)-3-(2-diazo-3-oxobutanyol)-1,1-dioxo-1$\lambda^6$,3-(and 1-oxo-1$\lambda^4$,3-) thiazolidine-4-carboxylates", J. Chem. Soc., Perkin Trans. 1, pp. 1067-1072 (1999).
Brown, E.M. et al., "Cloning and characterization of an extracellular Ca(2+) -Sensing receptor from bovine parathyroid" Nature, vol. 366. Dec. 9, 1993. pp. 575-580.

(Continued)

*Primary Examiner*—Deepak Rao
(74) *Attorney, Agent, or Firm*—Burton Rodney; Maureen S. Gibbons

(57) ABSTRACT

Trisubstituted heteroaromatic compounds having the structure

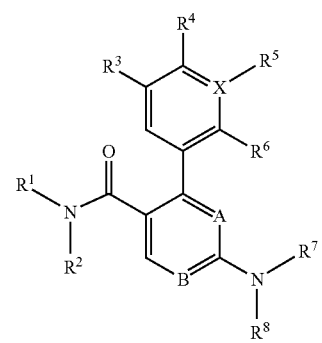

I are provided, wherein
X is C or N;
A and B are each independently CH or N, with the proviso that A and B cannot both be CH;
$R^1$ is Ar-L-;
$R^2$ is hydrogen or alkyl;
or $R^1$ and $R^2$ can be joined together to form a 4- to 7-membered cycloheteroalkyl ring;
$R^3$ to $R^8$, Ar and L are as defined herein. A method for using these compounds to treat diseases associated with abnormal bone or mineral homeostasis is also provided

16 Claims, No Drawings .

OTHER PUBLICATIONS

Bundgaard, H., Chapter 5: "Design and Application of Prodrugs", A Textbook of Drug Design and Development, Harwood Academic Publishers, publ., Krogsgaard-Larsen, P. et al., eds., pp. 113-191 (1991).

Bundgaard, H., ed., Design of Prodrugs, Elsevier Science Publishers B.V., publ. (1985) (table of contents).

Cagniant, P. et al., "No. 50. Sur la synthèse de quelques amines arylaliphatiques dérivées du β-méthyl-naphtalène", Bull. Soc. Chim. Fr., pp. 349-353 (1943).

Clay, R.J. et al., "A Safe, Economical Method for the Preparation of β-Oxo Esters[1]", Synthesis 1993, pp. 290-292.

Davis, F.A. et al., Tetrahedron Letters No. 52, 1978, pp. 51771-51774.

Edwards, J.P. et al., "Nonsteroidal Androgen Receptor Agonists Based on 4-(trifluoromethyl)-2H-pyrano[3,2-g ]quinolin-2-one", Bioorganic & Medicinal Chemistry Letters, vol. 9, pp. 1003-1008 (1999).

Gowen, M. et al., "Antagonizing the parathyroid calcium receptor stimulates parathyroid hormone secretion and bone formation in osteopenic rats", The Journal of Clinical Investigation, vol. 105, No. 11, pp. 1595-1604 (2000).

Greene, T.W. et al., Protecting Groups in Organic Synthesis, Third Edition, John Wiley & Sons, Inc., publ. (1999) (table of contents).

Hamann, L.G. et al., "Discovery of a Potent, Orally Active, Nonsteroidal Androgen Receptor Agonist: 4-Ethyl-1,2,3,4-tetrahydro-6-(trifluoromethyl)-8-pyridono[5,6-g]-quinoline (LG121071)", J. Med. Chem., vol. 42, pp. 210-212 (1999).

Lee, D.G., Chapter 11: "Phase Transfer Assisted Permanganate Oxidations", Oxidation in Organic Chemistry, Part D, Academic Press, publ., Trahanovsky, W.S., ed., pp. 147-204 (1982).

Neer, R.M. et al., "Effect of Parathyroid Hormone (1-34) on Fractures and Bone Mineral Density in Postmenopausal Women with Osteoporosis", The New England Journal of Medicine, vol. 344, No. 19, pp. 1434-1441 (2001).

Nemeth, E.F. et al., "The role of extracellular calcium in the regulation fo intracellular calcium and cell function". Cell Calcium (1990) vol. 11, pp. 319-321.

Norris, R.K. et al., "Kinetics and Stereochemistry of Elimination of Nitrous Acid from 1-p-Nitrophenyl-2-nitroethyl Derivatives", Aust. J. Chem., vol. 39, pp. 281-294 (1986).

Stewart, R., Chapter 1: "Oxidation by Permanganate", Oxidation in Organic Chemistry, Part A, Academic Press, publ., Wiberg, K.B., ed., pp. 1-68 (1965).

Wermuth, C.G. et al., Chapter 31: "Designing Prodrugs and Bioprecursors I: Carrier Prodrugs", The Practice of Medicinal Chemistry, Academic Press, publ., Wermuth, C.G., ed., pp. 671-696 (1996).

Whitfield, J.F. et al., "Parathyroid Hormone, Its Fragments and Their Analogs for the Treatment of Osteoporosis", Treat. Endocrinol., vol. 1, No. 3, pp. 175-190 (2002).

* cited by examiner

TRISUBSTITUTED HETEROAROMATIC COMPOUNDS AS CALCIUM SENSING RECEPTOR MODULATORS

CROSS-REFERENCE TO RELATED APPLICATION

This application claims the benefit of U.S. Provisional Application No. 60/473,904, filed May 28, 2003, which is incorporated herein by reference in its entirety

FIELD OF THE INVENTION

The present invention relates to novel trisubstituted heteroaromatic compounds which are modulators of the calcium sensing receptor, pharmaceutical compositions containing these compounds, and a method using these compounds to treat diseases or disorders associated with abnormal bone or mineral homeostasis.

BACKGROUND OF THE INVENTION

Certain cells in the body respond not only to chemical signals, but also to ions such as extracellular calcium ions ($Ca^{2+}$). Changes in the concentration of extracellular $Ca^{2+}$ (referred to herein as "$[Ca^{2+}]$") alter the functional responses of these cells. One such specialized cell is the parathyroid cell which secretes parathyroid hormone (PTH). PTH is the principal endocrine factor regulating $Ca^{2+}$ homeostasis in the blood and extracellular fluids.

PTH, by acting on bone and kidney cells, increases the level of $Ca^{2+}$ in the blood. This increase in $[Ca^{2+}]$ then acts as a negative feedback signal, depressing PTH secretion. The reciprocal relationship between $[Ca^{2+}]$ and PTH secretion forms the essential mechanism maintaining bodily $Ca^{2+}$ homeostasis.

Extracellular $Ca^{2+}$ acts directly on parathyroid cells to regulate PTH secretion. The existence of a parathyroid cell surface protein which detects changes in $[Ca^{2+}]$ has been confirmed (see Brown et al., Nature 366:574, 1993). In parathyroid cells, this protein, the calcium sensing receptor, acts as a receptor for extracellular Ca 2+, detects changes in the ion concentration of extracellular $Ca^{2+}$, and initiates a functional cellular response, PTH secretion.

Extracellular $Ca^{2+}$ influences various cell functions, as reviewed in Nemeth et al., Cell Calcium 11:319, 190. Specifically, the osteoclast in bone, the juxtaglomerular, proximal tubule cells in the kidney, the keratinocyte in the epidermis, the parafollicular cell in the thyroid, intestinal cells, and the trophoblast in the placenta, have the capacity to sense changes in $[Ca^{2+}]$. It has been suggested that cell surface calcium sensing receptors may also be present on these cells, imparting to them the ability to detect and to initiate or enable a response to changes in $[Ca^{2+}]$.

Accordingly, compounds which mimic the effects of extracellular $Ca^{2+}$ on a calcium sensing receptor molecule may be useful as calcium modulators which are active at $Ca^{2+}$ receptors. Such compounds could be useful in the treatment of various disease states characterized by abnormal levels of one or more components, e.g., polypetides, such as hormones, enzymes or growth factors, the expression and/or secretion of which is regulated or affected by activity at one or more $Ca^{2+}$ receptors. Target diseases or disorders for these compounds include diseases involving abnormal bone and mineral homeostasis.

Abnormal calcium homeostasis may be characterized by one or more of the following activities: abnormal increase or decrease in serum calcium; an abnormal increase or decrease in urinary excretion of calcium; an abnormal increase or decrease in bone calcium levels (for example, as assessed by bone mineral density measurements); an abnormal absorption of dietary calcium; an abnormal increase or decrease in the production and/or release of messengers which affect serum calcium levels, such as PTH and calcitonin; and an abnormal change in the response elicited by messengers which affect serum calcium levels.

In extensive animal experiments and in clinical trials, intermittent injection of low doses of PTH has been shown to be a safe and effective stimulator of bone formation (see Whitfiled J F, et al. (2002) Treat Endocrinol (2002) 1(3):175-190). A double blind, randomized, placebo-controlled trial in postmenopausal women, the PTH peptide fragment (1-34) was shown to reduce the risk of spine fractures and non-traumatic, non-spine fractures 65% and 54%, respectively (Neer R M, et al. (2001) N Engl J Med 344:1434-1441.). In contrast to the anabolic effects observed after intermittent administration, it is well documented that continuous exposure to the hormone results in increases in bone turnover with a subsequent loss in bone mass.

Other than applying a PTH peptide fragment, conceivably, one could make use of the endogenous stores of PTH in the parathyroid gland, in order to stimulate bone formation through the release of PTH.

Proof-of-principle for the calcilytic approach includes a study in osteopenic ovariectomized (OVX) rats in which oral administration of a calcilytic agent NPS-2143 (Gowen M, et al. (2000) J. Clin. Invest. 105:1595-1604) resulted in an increase in bone mass in the presence of an anti-resorptive agent. Intravenous bolus injection of NPS-2143 resulted in a transient increase in serum PTH compatible with the anabolic profile of the hormone. These results indicate that calcilytic agents can serve as a novel class of anabolic agents for the treatment of established osteoporosis.

Thus, the identification of compounds which demonstrate activity as calcium sensing receptor modulators, preferably calcium sensing receptor antagonists, would be of significant value for the treatment of diseases or disorders associated with abnormal bone or mineral homeostasis.

SUMMARY OF THE INVENTION

In accordance with the present invention, compounds are provided which are capable of modulating the function of a calcium sensing receptor, which compounds are preferably antagonists of the calcium sensing receptor, and have the general formula I

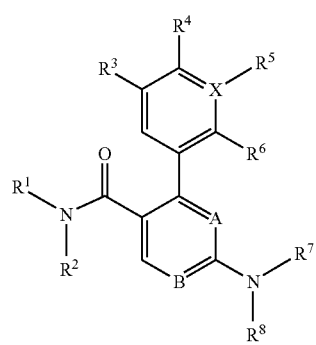

wherein
X is C or N;
A and B are each independently CH or N, with the proviso that A and B cannot both be CH;
$R^1$ is Ar-L-;
$R^2$ is hydrogen or alkyl;
or $R^1$ and $R^2$ can be joined together to form a 4- to 7-membered cycloheteroalkyl ring;
Ar is aryl or heteroaryl;
L is a linking group containing 1 to 6 atoms in a linear chain, which may be all carbons or may have one or two heteroatoms in the chain including N, O, and S, and may be unsubstituted or substituted with one, two, three or four substituents which can be alkyl, cycloalkyl, haloalkyl, oxo (=O), alkoxy, aryl, arylalkyl, hydroxy, heteroaryl or cycloheteroalkyl.
$R^3$, $R^5$, and $R^6$ are each independently hydrogen, alkyl, cycloalkyl, alkenyl, alkynyl, alkoxy, hydroxy, halo, haloalkyl, haloalkoxy, nitro, cyano, trifluoromethyl, trifluoromethoxy, amino, alkylamino, thiol, alkylthio, alkylsulfinyl, or alkylsulfonyl;
$R^4$ is alkyl, cycloalkyl, alkenyl, alkynyl, alkoxy, hydroxy, halo, haloalkyl, haloalkoxy, nitro, cyano, trifluoromethyl, trifluoromethoxy, amino, alkylamino, thiol, alkylthio, alkylsulfinyl, or alkylsulfonyl;
$R^7$ is alkyl, cycloalkyl, cycloalkylalkyl, cycloheteroalkyl, cycloheteroalkylalkyl, arylalkyl, heteroarylalkyl, arylaminoalkyl, or arylthioalkyl;
$R^8$ is hydrogen or alkyl;
or $R^7$ and $R^8$ can be joined together to form a 4- to 7-membered cycloheteroalkyl ring.

The definition of formula I above being inclusive of all pharmaceutically acceptable salts, stereoisomers and prodrug esters of formula I.

The compounds of formula I function as modulators of the calcium sensing receptor. Preferably, the compounds of formula I exhibit activity as antagonists of the calcium sensing receptor and may be used in the treatment of diseases or disorders associated with calcium sensing receptor activity, such as abnormal bone and mineral homeostasis, particularly, hypoparathyroidism, osteosarcoma, chondrosarcoma, periodontal disease, fracture healing, osteoarthritis, Paget's disease, osteopenia, glucocorticoid-induced osteoporosis, osteomalacia, osteoporosis, metastatic bone disease or joint replacement.

The present invention provides for compounds of formula I, pharmaceutical compositions employing such compounds and for methods of using such compounds. The present invention also provides a pharmaceutical composition comprising a therapeutically effective amount of a compound of formula I, alone or in combinations with a pharmaceutically acceptable carrier.

Further, in accordance with the present invention, a method is provided for preventing, inhibiting or treating the progression or onset of diseases or disorders associated with abnormal bone and mineral homeostasis, such as hypoparathyroidism, osteosarcoma, chondrosarcoma, periodontal disease, fracture healing, osteoarthritis, Paget's disease, osteopenia, glucocorticoid induced osteoporosis, osteomalacia, osteoporosis, metastatic bone disease or joint replacement, wherein a therapeutically effective amount of a compound of formula I is administered to a mammalian, i.e., a human patient or a dog or cat in need of treatment.

The compounds of the invention can be used alone, in combination with other compounds of the present invention, or in combination with one or more other agent(s) active in the therapeutic areas mentioned herein.

In addition, a method is provided for preventing, inhibiting or treating the diseases as defined above and hereinafter, wherein a therapeutically effective amount of a combination of a compound of formula I and another type of therapeutic agent, is administered, concurrently or sequentially, to a mammalian species, for example, a human patient, dog or cat in need of treatment.

Preferred are compounds of formula I wherein:
$R^1$ is Ar-L-;
$R^2$ is hydrogen;
or $R^1$ and $R^2$ can be joined together to form an aryl-substituted piperidinyl ring or a benzofused piperidinyl ring;
Ar is phenyl;
L is alkylene or Oalkylene;
$R^3$, $R^5$, and $R^6$ are each independently hydrogen, alkyl, alkoxy, hydroxy, halo, haloalkyl, haloalkoxy, trifluoromethyl, or trifluoromethoxy;
$R^4$ is alkyl, alkoxy, hydroxy, halo, haloalkyl, haloalkoxy, trifluoromethyl, or trifluoromethoxy;
$R^7$ is alkyl, cycloalkylalkyl, arylalkyl, or heteroarylalkyl;
$R^8$ is hydrogen or alkyl;
or $R^7$ and $R^8$ can be joined together to form a pyrrolidinyl or piperidinyl ring;
X is C or N;
A and B are each N; or A is N and B is C; or A is C and B is N.

Examples of preferred compounds of the invention include the following compounds:

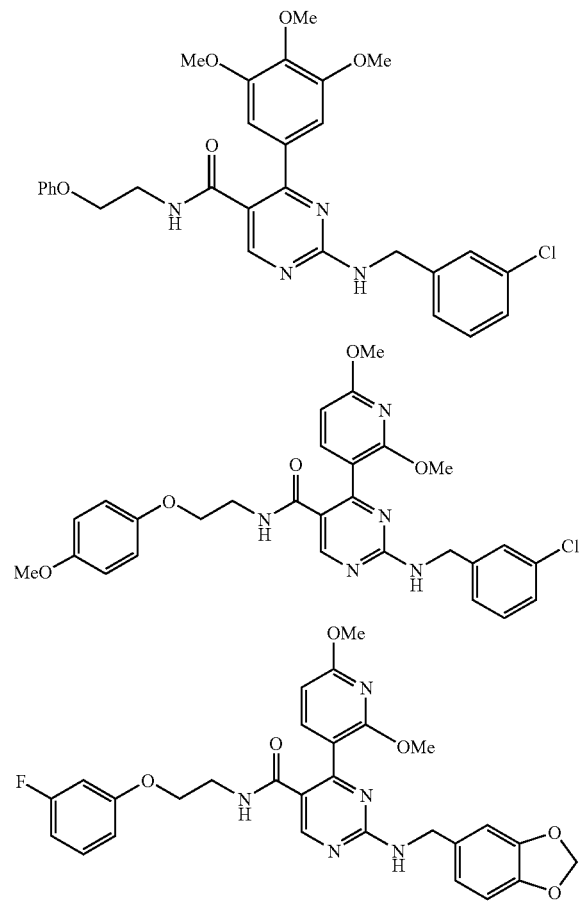

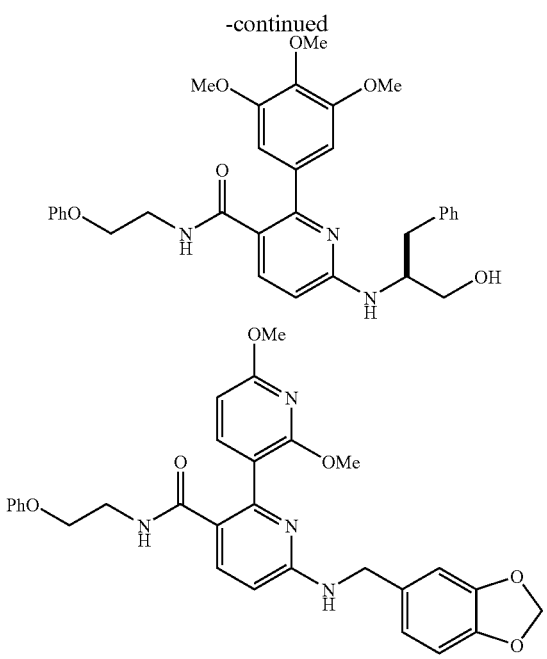

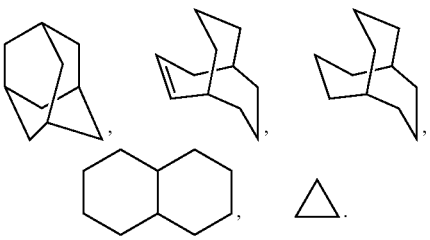

DETAILED DESCRIPTION OF THE INVENTION

The following definitions apply to the terms as used throughout this specification, unless otherwise limited in specific instances.

The term "alkyl" or "lower alkyl" as employed herein, alone or as part of another group, includes both straight and branched chain hydrocarbons, containing 1 to 12 carbons, preferably 1 to 8 carbons, more preferably 1 to 4 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like. Alkyl may be optionally substituted with one, two, three or four substituents (which may be the same or different) commonly attached to such chains, such as, but not limited to halo, for example F, Br, Cl or I or $CF_3$, alkyl, alkoxy, aryl, aryloxy, aryl(aryl) or diaryl, arylalkyl, arylalkyloxy, alkenyl, alkynyl, cycloalkyl, cycloalkenyl, cycloalkylalkyl, cycloalkylalkyloxy, optionally substituted amino, hydroxy, hydroxyalkyl, acyl, oxo, alkanoyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, alkoxycarbonyl, alkylaminocarbonyl, nitro, cyano, thiol, haloalkyl, trihaloalkyl, alkylthio, carboxyl, and the like.

Unless otherwise indicated, the term "cycloalkyl" as employed herein alone or as part of another group includes saturated or partially unsaturated (containing 1 or more double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl, Cycloalkyl may be optionally substituted with one to four substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol and/or alkylthio and/or any of the substituents included for "alkyl."

The term "halogen" or "halo" as used herein alone or as part of another group refers to chlorine, bromine, fluorine, and iodine.

Unless otherwise indicated, the term "aryl", "aromatic" or "Ar" as employed herein alone or as part of another group refers to monocyclic and polycyclic (conjugated or fused) aromatic groups containing 5 to 14 carbons in the ring portion (such as phenyl or naphthyl, including 1-naphthyl and 2-naphthyl) and may optionally include one to three additional rings fused to a carbocyclic ring or a heterocyclic ring (such as aryl, cycloalkyl, heteroaryl or cycloheteroalkyl rings, for example

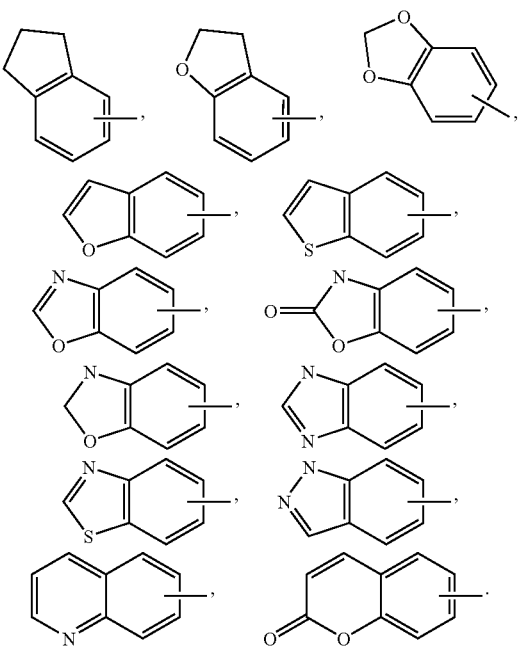

Aryl groups may be optionally substituted through available carbon atoms with one to four substituents, such as hydrogen, halo, haloalkyl, alkyl, alkoxy, haloalkoxy, alkenyl, trifluoromethyl, trifluoromethoxy, alkynyl, cycloalkylalkyl, cycloheteroalkyl, cycloheteroalkylalkyl, aryl, heteroaryl, arylalkyl, heteroarylalkyl, aryloxy, aryloxyalkyl, alkoxyalkyl, arylalkoxy, alkoxycarbonyl, aryloxycarbonyl, arylalkoxycarbonyl, arylalkenyl, heteroarylalkenyl, heteroarylheteroaryl, heteroaryloxy, heteroarylalkoxy, heteroaryloxyalkyl, aminocarbonylalkyl, aminocarbonylaryl, arylthio, arylalkylthio, heteroarylalkylthio, arylazo, hydroxy, nitro, cyano, carboxyl, carboxyalkoxy, alkoxycarbonylalkoxy, amino, substituted amino, wherein the amino includes 1 or 2 substituents such as alkyl, aryl (or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, alkylsulfonyl, arylsulfonyl, heteroarylsulfonyl, cycloheteroalkylsulfonyl, alkylsulfinyl, arylsulfinyl, arylsulfinylalkyl, arylsulfonylamino, arylsulfonaminocarbonyl and/or any of the alkyl substituents set out herein.

The term "fused" refers to aromatic or heteroaromatic rings that share a pair of carbon atoms, and includes multiple fused aromatic or heteroaromatic rings, for example naphthalene or naphthyridine.

Unless otherwise indicated, the term "heteroaryl" or "heteroaromatic" as used herein alone or as part of another group refers to a 5- or 6-membered aromatic ring which includes 1, 2, 3 or 4 heteroatoms such as nitrogen, oxygen, or sulfur, and such rings fused to an aryl, cycloalkyl, heteroaryl or cycloheteroalkyl ring (e.g. benzothiophenyl, indole), and includes possible N-oxides. Heteroaryl may be optionally substituted with one to four substituents such as any of the alkyl or aryl substituents set out above. Examples of heteroaryl groups include the following:

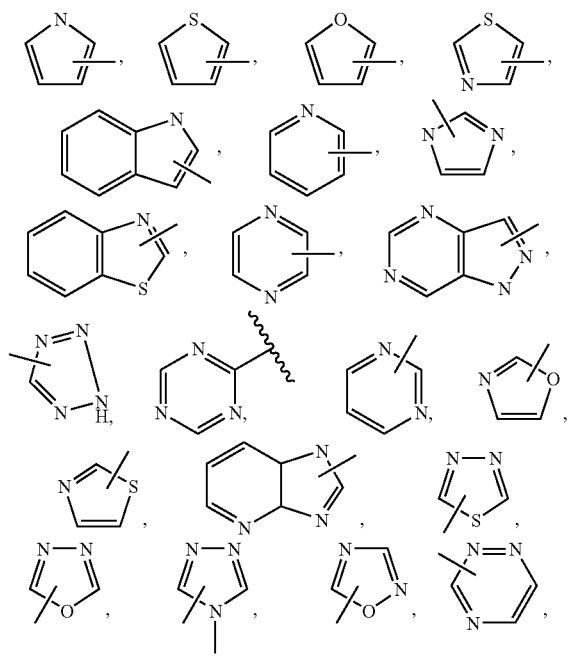

and the like.

Unless otherwise indicated, the term "cycloheteroalkyl" as used herein alone or as part of another group refers to a 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_p$ (where p is 1, 2 or 3), such as

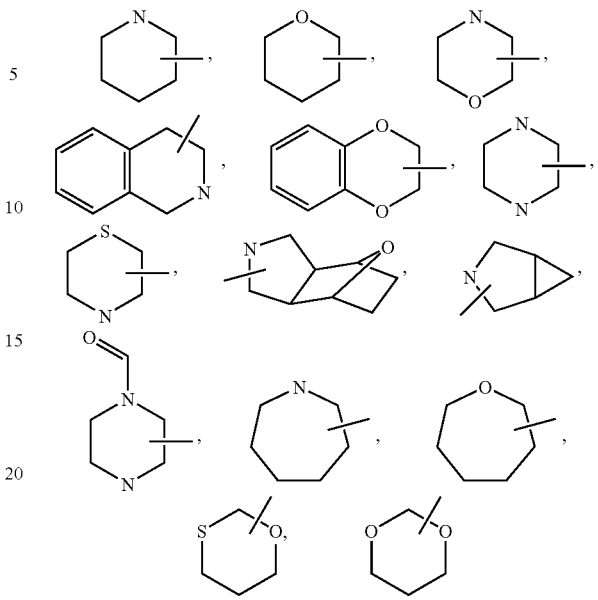

and the like. The above groups may include 1 to 4 substituents such as alkyl, halo, oxo and/or any of the substituents for alkyl or aryl set out herein. In addition, any of the cycloheteroalkyl rings can be fused to a cycloalkyl, aryl, heteroaryl or cycloheteroalkyl ring.

The term "cycloheteroalkylalkyl" as used herein alone or as part of another group refers to cycloheteroalkyl groups as defined above linked through a C atom or heteroatom to a $(CH_2)_p$ chain.

The term "heteroarylalkyl" or "heteroarylalkenyl" as used herein alone or as part of another group refers to a heteroaryl group as defined above linked through a C atom or heteroatom to a —$(CH_2)_p$— chain, alkylene or alkenylene as defined above.

Unless otherwise indicated, the term "lower alkenyl" or "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, and may optionally include an oxygen or nitrogen in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio and/or any of the substituents for alkyl set out herein.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, and may optionally include an oxygen or nitrogen in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the substituents for alkyl set out herein.

The L linking group includes alkylene groups, as defined herein, each of which may optionally include an oxygen, nitrogen and/or sulfur in the normal chain, which may optionally include 1, 2, or 3 substituents which include alkyl, alkenyl, halogen, cyano, hydroxy, alkoxy, amino, thioalkyl, keto, $C_3$-$C_6$ cycloalkyl, alkylcarbonylamino or alkylcarbonyloxy; the alkyl substituent may be an alkylene moiety of 1 to 6 carbons which may be attached to one or two carbons in the alkylene group to form a cycloalkyl group therewith.

Examples of L alkylene groups include

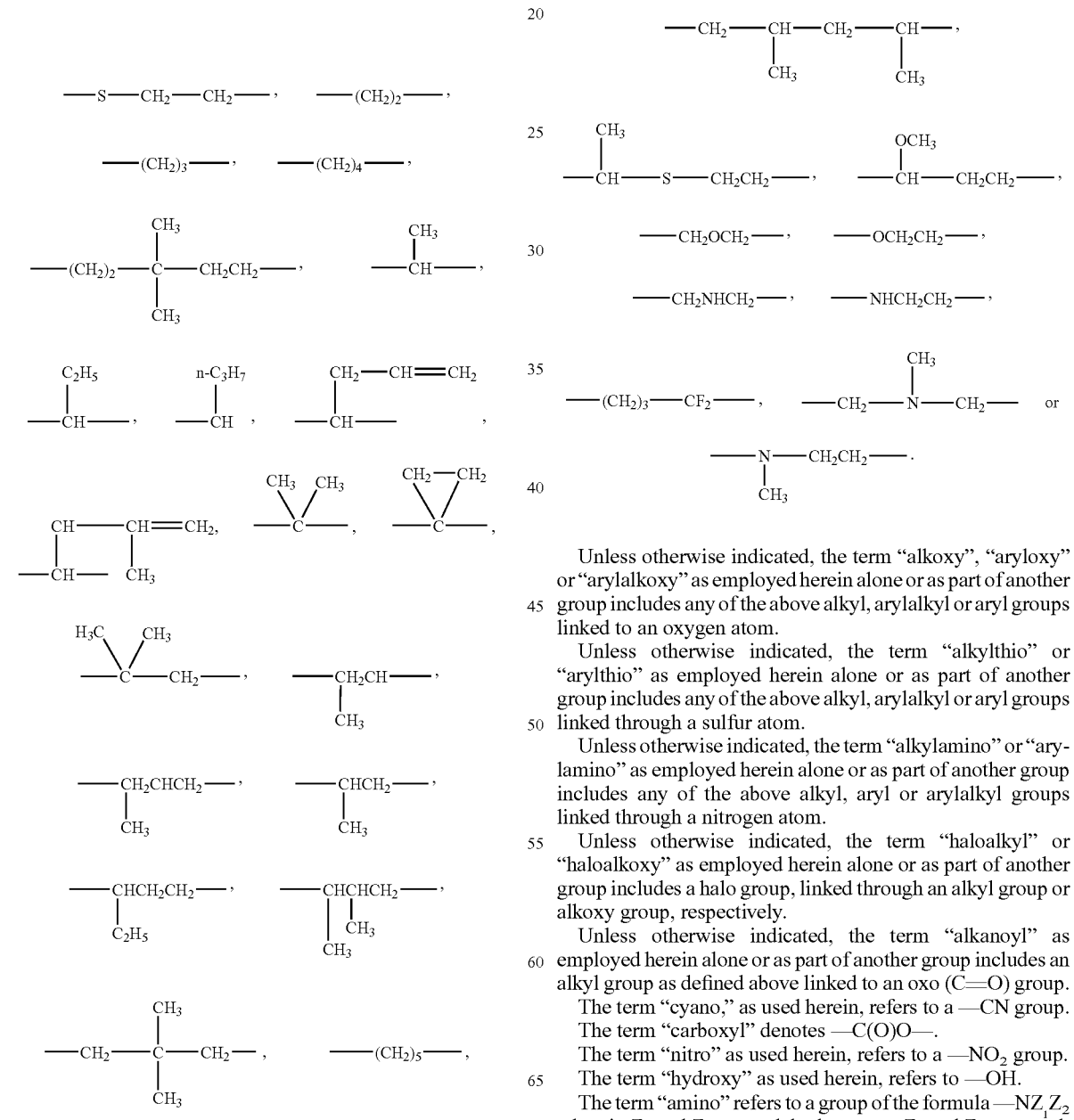

Unless otherwise indicated, the term "alkoxy", "aryloxy" or "arylalkoxy" as employed herein alone or as part of another group includes any of the above alkyl, arylalkyl or aryl groups linked to an oxygen atom.

Unless otherwise indicated, the term "alkylthio" or "arylthio" as employed herein alone or as part of another group includes any of the above alkyl, arylalkyl or aryl groups linked through a sulfur atom.

Unless otherwise indicated, the term "alkylamino" or "arylamino" as employed herein alone or as part of another group includes any of the above alkyl, aryl or arylalkyl groups linked through a nitrogen atom.

Unless otherwise indicated, the term "haloalkyl" or "haloalkoxy" as employed herein alone or as part of another group includes a halo group, linked through an alkyl group or alkoxy group, respectively.

Unless otherwise indicated, the term "alkanoyl" as employed herein alone or as part of another group includes an alkyl group as defined above linked to an oxo (C=O) group.

The term "cyano," as used herein, refers to a —CN group.
The term "carboxyl" denotes —C(O)O—.
The term "nitro" as used herein, refers to a —$NO_2$ group.
The term "hydroxy" as used herein, refers to —OH.
The term "amino" refers to a group of the formula —$NZ_1Z_2$ wherein $Z_1$ and $Z_2$ are each hydrogen, or $Z_1$ and $Z_2$ may each independently be alkyl, aryl or any of the substituents described for alkyl or aryl above.

The compounds of formula I can be present as salts, which are also within the scope of this invention. Pharmaceutically acceptable (i.e., non-toxic, physiologically acceptable) salts are preferred. If the compounds of formula I have, for example, at least one basic center, they can form acid addition salts. These are formed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methyl- or p-toluenesulfonic acid. Corresponding acid addition salts can also be formed having, if desired, an additionally present basic center. The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di-, or tri-lower alkylamine, for example ethyl, tertbutyl, diethyl, diisopropyl, triethyl, tributyl or dimethylpropylamine, or a mono-, di-, or trihydroxy lower alkylamine, for example mono-, di-, or triethanolamine. Corresponding internal salts may furthermore be formed. Salts which are unsuitable for pharmaceutical uses but which can be employed, for example, for the isolation or purification of free compounds of formula I or their pharmaceutically acceptable salts, are also included.

Preferred salts of the compounds of formula I which contain a basic group include monohydrochloride, hydrogen sulfate, methanesulfonate, phosphate or nitrate.

Preferred salts of the compounds of formula I which contain an acid group include sodium, potassium and magnesium salts and pharmaceutically acceptable organic amines.

The term "modulator" refers to a chemical compound with capacity to either enhance (e.g., "agonist" activity) or inhibit (e.g., "antagonist" activity) a functional property of biological activity or process (e.g., enzyme activity or receptor binding); such enhancement or inhibition may be contingent on the occurrence of a specific event, such as activation of a signal transduction pathway, and/or may be manifest only in particular cell types.

The term "prodrug esters" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates and the like.

Any compound that can be converted in vivo to provide the bioactive agent (i.e., the compound of formula I) is a prodrug within the scope and spirit of the invention.

Various forms of prodrugs are well known in the art. A comprehensive description of prodrugs and prodrug derivatives are described in:

*The Practice of Medicinal Chemistry*, Camille G. Wermuth et al., Ch 31, (Academic Press, 1996);

*Design of Prodrugs*, edited by H. Bundgaard, (Elsevier, 1985); and

*A Textbook of Drug Design and Development*, P. Krogsgaard-Larson and H. Bundgaard, eds. Ch 5, pgs 113-191 (Harwood Academic Publishers, 1991).

Said references are incorporated herein by reference.

An administration of a therapeutic agent of the invention includes administration of a therapeutically effective amount of the agent of the invention. The term "therapeutically effective amount" as used herein refers to an amount of a therapeutic agent to treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration. Thus, it is not useful to specify an exact effective amount in advance.

All stereoisomers of the compounds of the instant invention are contemplated, either in admixture or in pure or substantially pure form. The compounds of the present invention can have asymmetric centers at any of the carbon atoms including any one of the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatography or fractional crystallization.

The compounds of formula I of the invention can be prepared as shown in the following reaction schemes and description thereof, as well as relevant published literature procedures that may be used by one skilled in the art. Exemplary reagents and procedures for these reactions appear hereinafter and in the working Examples.

Compounds of the formula I, where A=B=N, can be prepared by reacting sulfoxide II with an appropriately substituted amine ($R^7R^8NH$), preferably in excess, in a solvent such as THF or DMF, under microwave irradiation, or neat, and preferably under heating (e.g. between 50° C. and 150° C.) (Scheme 1), employing a molar ratio of amine:II within the range from about 1:1 to about 1000:1, preferably from about 1:1 to about 10:1.

Sulfoxide II can arise from first coupling of the carboxylic acid III to the appropriate amine ($R^1R^2NH$) through the reaction of standard acylation reagents such as 1-(3-dimethylaminopropyl)-3-ethylcarbodiimide (EDC) and 1-hydroxybenztriazole (HOBt), or bromotripyrrolidinophosphonium hexafluorophosphate (PyBroP) as known in the literature, then mono-oxidation of the sulfide functional group with, for example, an oxaziridine reagent (e.g. see Davis, F. A., et al., *Tetrahedron Lett.*, 1978, 5171-4) or by various standard oxidation methods known in the literature (e.g. Stewart, R. In *Oxidation in Organic Chemistry*; Wiberg, K. B., Ed.; Academic Press: New York, 1965; Lee, D. G. In Oxidation in *Oxydation in Organic Chemistry*; Trahanovsky, W. S., Ed.; Academic Press: New York, 1982; Arndt, D. In Methoden der Organischen Chemie (Houben-Weyl) 4$^{th}$ Ed.; Muller, E., Ed., Thieme: Stuttgart, 1975; Vol. E 4/1b; and, Betts, M. J. *J. Chem. Soc., Perkin Trans.* 1, 1999, 1067-1072). Alternatively, carboxylic acid III may undergo oxidation to give sulfoxide IV, followed by amine displacement to give V, then amide coupling to provide compounds of formula I.

Compounds of the formula I, where A=B=N, can also be prepared by metal-catalyzed (e.g. using a Pd or Ni catalyst) coupling of the pyrimidyl chloride VI with the appropriately functionalized organometallic reagent XVII via Stille or Suzuki conditions. In the organometallic reagent XVII, M can be variety of metal-containing functional groups, e.g. $B(OH)_2$, $SnBu_3$, ZnX, ZnBr, or MgX, where X is Br, Cl, or I, but is preferably $B(OH)_2$.

to about 150° C., preferably from about 50 to about 100° C., employing a molar ratio of S-methylthiourea:IX within the range from about 0.5:1 to about 100:1, preferably from about 0.5:1 to about 3:1, followed by hydrolysis/deprotection of the ester protecting group (Scheme 2). Suitable protecting groups or references thereto can be found, along with the appropriate deprotection conditions, in Greene, Theodora W.; Wuts, Peter G. M. *Protective Groups in Organic Synthesis*, 3$^{rd}$ ed.; Wiley

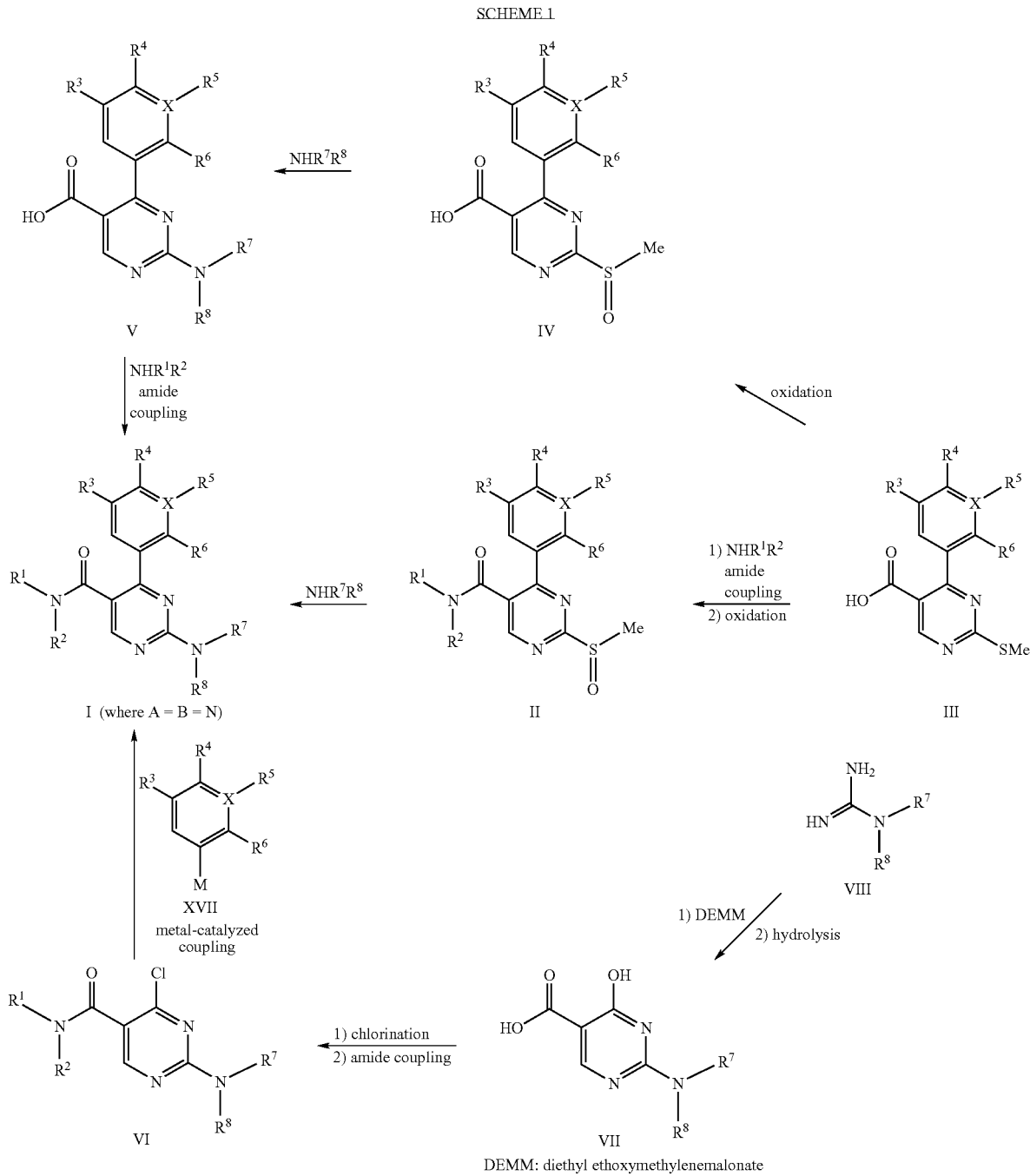

SCHEME 1

DEMM: diethyl ethoxymethylenemalonate

Compounds of formula III may be prepared via cyclization of compounds of the formula IX upon treatment with S-methylthiourea, at a temperature within the range from about 20

& Sons: New York, 1999. Preferably, PG is a simple alkyl group such as methyl, ethyl, or tert-butyl. Compounds of the formula IX may be prepared from the β-ketoester X via treatment with dimethylformamide dimethyl acetal (DM-FDA) at a temperature within the range from about 20 to about 150° C., preferably from about 50 to about 120° C., employing a molar ratio of DMFDA:X within the range from about 1:1 to about 100:1, preferably from about 1:1 to about 3:1.

The synthesis of the requisite β-ketoester X can be accomplished by transformation of the appropriate aryl or heteroaryl carboxylic acid XI (see Synthesis, 1993, 290-292). Compounds of the formula XI are either commercially available, known in the literature, or can be prepared according to the synthesis of similar analogs prepared in the literature.

from about 1:1 to about 5:1, at a temperature within the range from about 20° C. to about 150° C., preferably from about 20° C. to about 80° C.

Resin-bound sulfone XII may be prepared by standard oxidation conditions, as mentioned herein, from the resin-bound sulfide XIII. Compounds of the formula XIII are available via deprotection followed by amide formation of the suitably protected ester XIV under conditions described herein. Similar to the solution phase method described in Scheme 2, formation of the resin-bound XIV compounds may be accomplished by reaction of the resin-bound thiourea derivative XV with the appropriate β-ketoester derivative IX,

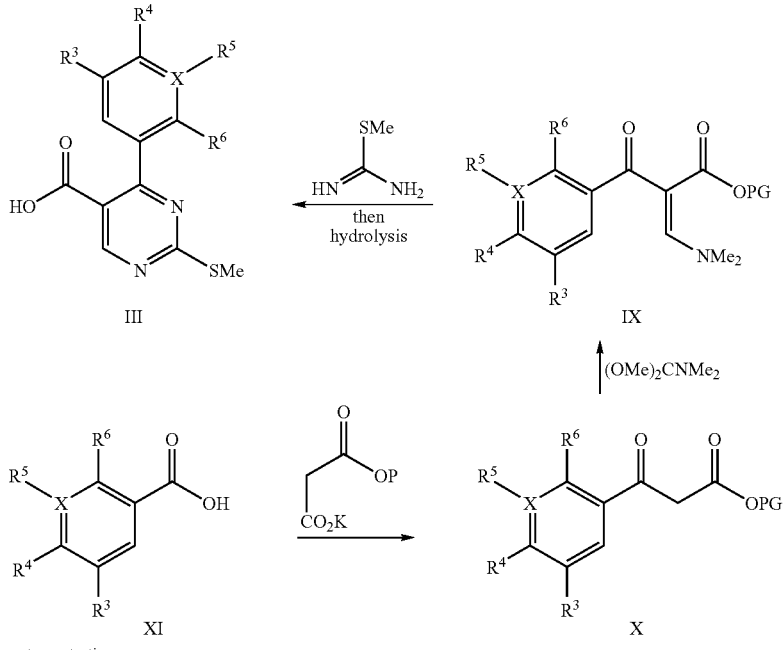

PG = an ester protecting group

Compounds of the formula I, where A=B=N, can also be prepared by a solid phase route as outlined in Scheme 3. Synthesis of the formula I compounds can be accomplished by reaction of the appropriate amine ($R^7R^8NH$) with the resin-bound sulfone XII, employing a molar ratio of amine:XII within the range from about 1:1 to about 100:1, preferably employing a molar ratio of IX:XV within the range from about 0.5:1 to about 100:1, preferably from about 1:1 to about 5:1, at a temperature within the range from about 20° C. to about 150° C., preferably from about 20° C. to about 80° C. The resin XV may be prepared from a functionalized resin, e.g. Merrifield's peptide resin, via treatment with thiourea.

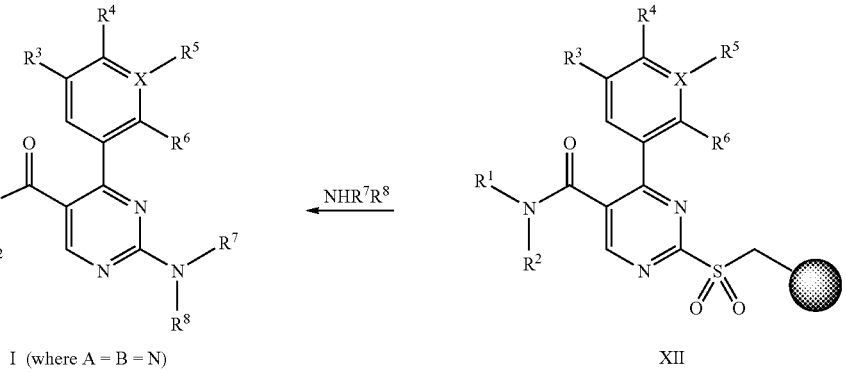

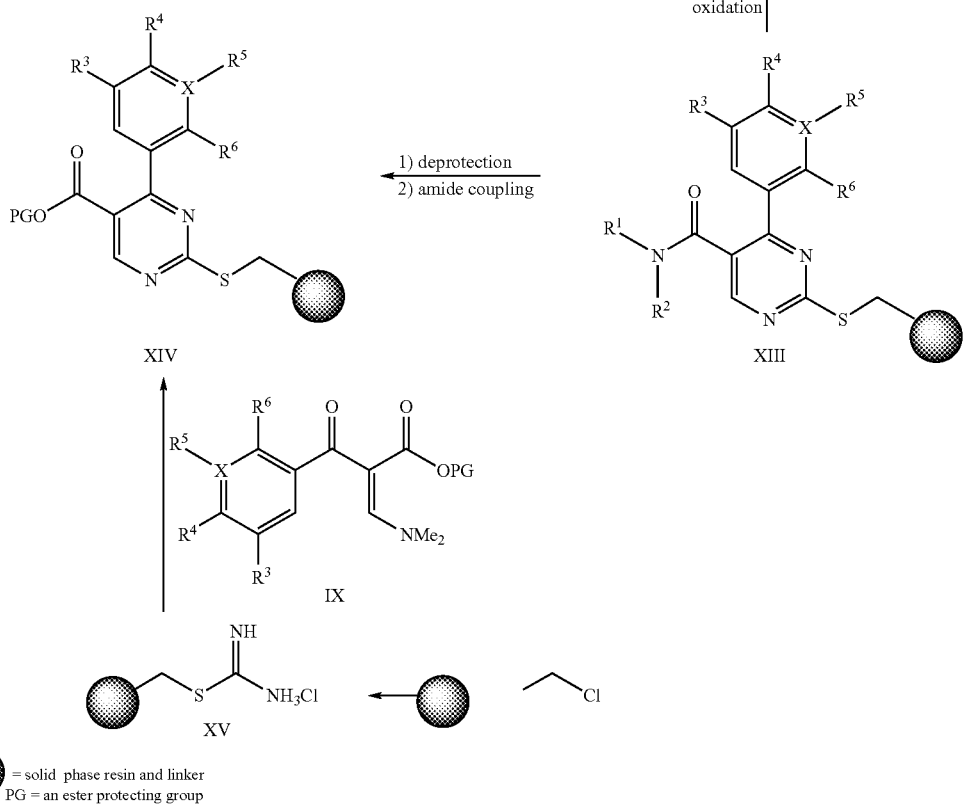

Compounds of the formula I, where A=N and B=CH, can be prepared by the methods described in Scheme 4. The chloropyridine XVI, where W=NR$^1$R$^2$, can be reacted with the appropriate NHR$^7$R$^8$ amine at a temperature within the range from about 20 to about 200° C., preferably from about 20 to about 150° C., employing a molar ratio of amine:XVI within the range from about 0.5:1 to about 100:1, preferably from about 1:1 to about 5:1, to give compounds of the formula I; or, when W=OPG, amine displacement may be followed by conversion of the ester into the appropriate amide. The ester to amide conversion may be accomplished by standard methods, and the amine displacement of the chloropyridine may be accomplished under similar conditions to the chloropyrimidine displacements (where A=B=N).

Compounds of the formula XVI can be prepared by metal-catalyzed arylation of the dichloropyridine XVIII with the appropriately functionalized organometallic reagent XVII at a temperature within the range from about 20 to about 200° C., preferably from about 50 to about 100° C., employing a molar ratio of XVII:XVIII within the range from about 1:1 to about 20:1, preferably from about 1:1 to about 3:1.

Preparation of the dichloropyridine XVIII can be accomplished either by standard amidation (where W=NR$^1$R$^2$) of 2,6-dichloronicotinic acid, or by simple esterification (where W=OPG) of the reagent.

SCHEME 4

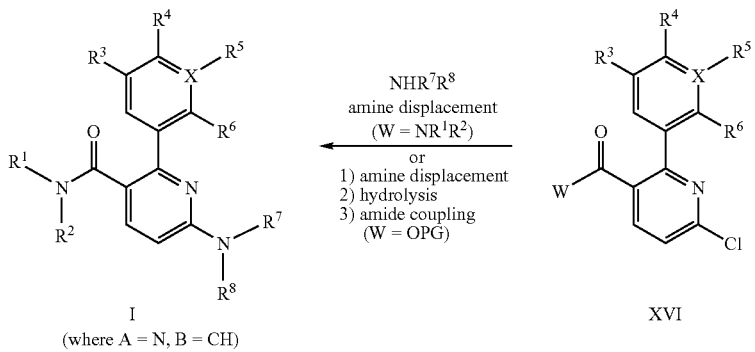

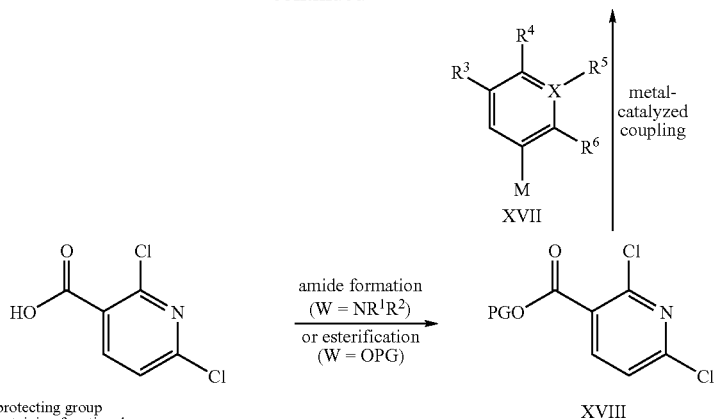

Compounds of the formula I, where A=CH and B=N, may be prepared by metal-catalyzed arylation of the appropriately functionalized halopyridine XXI under conditions described herein (Scheme 5). When Q=SMe, providing compounds XX, compounds of the formula I may be prepared by oxidation of the sulfide to either a sulfoxide or sulfone, followed by amine displacement. When Q is the appropriate amine substituent $NR^7R^8$, compounds of the formula I arise directly from arylation of XIX with the appropriate organometallic reagent XVII, at a temperature within the range from about 20 to about 200° C., preferably from about 50 to about 100° C., employing a molar ratio of XVII:XIX within the range from about 1:1 to about 20:1, preferably from about 1:1 to about 3:1. Halopyridines XIX can be prepared by halogenation of the pyridines XXI, typically upon reaction with a strong base such as butyllithium or LDA, preferably at a low temperature (e.g. −100 to −40° C.), followed by treatment with a halogenating reagent (e.g. N-chlorosuccinimide, N-bromosuccinimide, $Br_2$, or $I_2$). For compounds of the invention, Y is preferably I or Br.

Compounds of the formula XXI can be prepared by displacement on the pyridine XXII either with the appropriate amine (where $Q=NR^7R^8$), at a temperature within the range from about 20 to about 200° C., preferably from about 20 to about 150° C., employing a molar ratio of amine:XXII within the range from about 0.5:1 to about 100:1, preferably from about 1:1 to about 5:1, or NaSMe (where Q=SMe), at a temperature within the range from about 20 to about 150° C., preferably from about 20 to about 50° C., employing a molar ratio of NaSMe:XXII within the range from about 1:1 to about 100:1, preferably from about 1:1 to about 5:1. Preparation of amides of the formula XXII may be accomplished by standard amide coupling of 6-chloronicotinic acid with the appropriate $NR^1R^2$ amine.

SCHEME 5

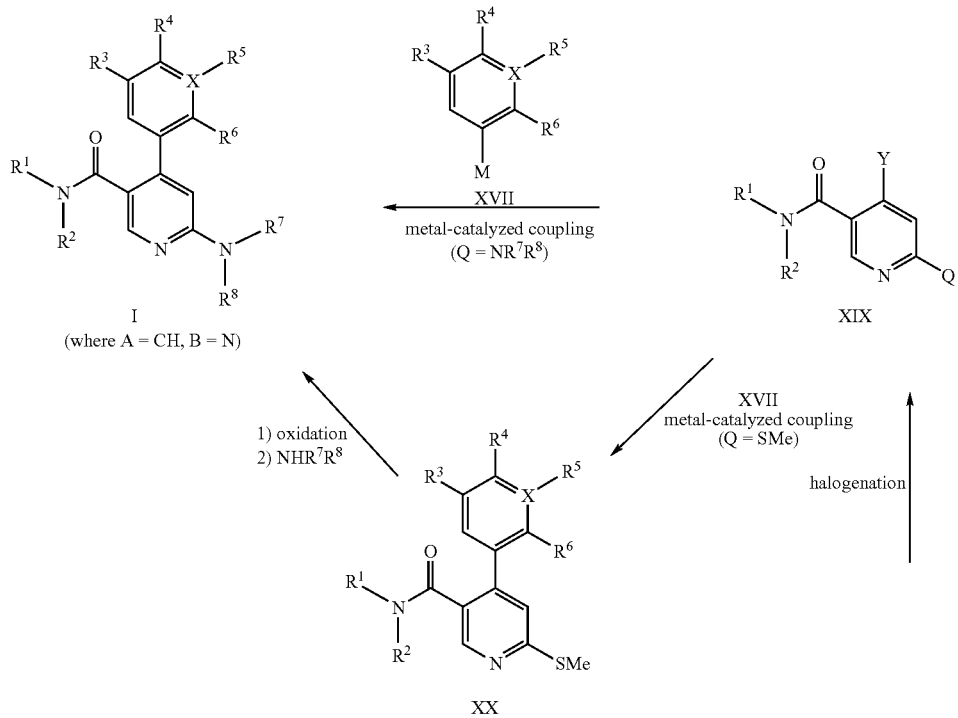

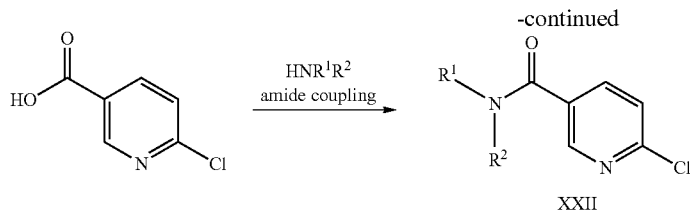 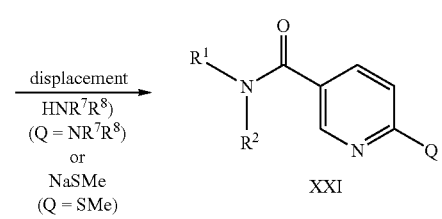

M = a metal-containing functional group
Y = Cl, Br, or I

Utilities and Combinations

A. Utilities

Diseases or disorders which can be treated by modulating calcium sensing receptor activity can be identified based on the functional responses of cells regulated by calcium receptor activity. Functional responses of cells regulated by the calcium sensing receptor are known in the art, including parathyroid hormone ("PTH") secretion by parathyroid cells, calcitonin secretion by C-cells, bone reabsorption by osteoclasts and $Ca^{2+}$ secretion by kidney cells.

The compounds of the present invention preferably function as modulators of the calcium sensing receptor, particularly as antagonists of the calcium sensing receptor. Accordingly, the compounds of the invention may be used to stimulate a functional response by parathyroid cells whereby such cells release PTH, preferably a transient release of PTH. Thus, the compounds of the present invention may be used in the treatment of diseases or disorders which can be affected by modulating one or more activities or functions of a calcium sensing receptor, wherein treatment comprises prevention, partial alleviation or cure of the condition or disorder. Modulation may occur locally, for example with certain tissues of the subject, or more extensively throughout a subject being treated for such a condition or disorder.

The compounds of the present invention can be administered animals, including humans, for the treatment of a variety of conditions and disorders, including, but not limited to bone and mineral-related diseases or disorders, (e.g., hypoparathyroidism, osteosarcoma, chondrosarcoma, periodontal disease, fracture healing, osteoarthritis, Paget's disease, osteopenia, glucocorticoid induced osteoporosis, osteomalacia and osteoporosis); metastatic bone disease; joint replacement; diseases involving excess water reabsorption by the kidney, such as syndrome of inappropriate ADA secretion (SIADH), cirrhosis, congestive heart failure and nephrosis; hypertension; diseases involving abnormally low serum parathyroid levels; preventing and/or decreasing renal toxicity from cationic antibiotics (e.g., amionglycoside antibiotics); renal osteodystrophy; gut motility disorders, such as diarrhea and spastic colon, GI ulcer diseases; GI diseases with excessive calcium absorption; sarcoidosis; autoimmune diseases and organ transplant rejection; inflammatory diseases, such as asthma, rheumatoid arthritis, inflammatory bowel disease, transplant rejection, and chronic obstructive pulmonary disease; and diseases caused by excess gastric acid secretion.

B. Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other compounds of the invention, or in combination with one or more other therapeutic agent(s) or other pharmaceutically active materials.

The compounds of the present invention may be employed in combination with other modulators of the calcium sensing receptor or other suitable therapeutic agents useful in the treatment of the aforementioned disorders including anti-osteoporosis agents, cholesterol/lipid lowering agents, growth promoting agents and/or progesterone receptor agonists.

Examples of suitable anti-osteoporosis agents for use in combination with the compounds of the present invention include bisphosphonates (e.g., alendronate, risedronate, ibandronate and zolendrate) parathyroid hormone, PTH fragment, calcitonins, RANK ligand antagonists, TRAP inhibitors and AP-1 inhibitors.

Examples of suitable cholesterol/lipid lowering agents for use in combination with the compounds of the present invention include HMG-CoA reductase inhibitors (e.g., pravastatin, lovastatin, atorvastatin, simvastatin, NK-104 (a.k.a. itavastatin, or nisvastatin or nisbastatin) and ZD-4522 (a.k.a. rosuvastatin, or atavastatin or visastatin)).

Examples of suitable growth promoting agents for use in combination with the compounds of the present invention include growth hormone secretagogues, such as GHRP-6, GHRP-1 (as described in U.S. Pat. No. 4,411,890 and publications WO 89/07110 and WO 89/07111), GHRP-2 (as described in WO 93/04081), NN703 (Novo Nordisk), LY444711 (Lilly), MK-677 (Merck), CP424391 (Pfizer) and B-HT920, or with growth hormone releasing factor and its analogs or growth hormone and its analogs or somatomedins including IGF-1 and IGF-2, or with alpha-adrenergic agonists, such as clonidine or serotonin 5-$HT_{1D}$ agonists, such as sumatriptan, or agents which inhibit somatostatin or its release, such as physostigmine and pyridostigmine.

Examples of suitable progesterone receptor agonists for use in combination with the compounds of the present invention include levonorgestrel and medroxyprogesterone acetate (MPA).

The compounds of the present invention may further be used in combination with modulators of bone resorption (e.g., estrogen); selective estrogen receptor modulators (e.g., tamoxifen, lasofoxifene, TSE-424 and raloxifene); or selective androgen receptor modulators, such as those disclosed in Edwards, J. P. et al., *Bio. Med. Chem. Let.*, 9, 1003-1008 (1999) and Hamann, L. G. et al., *J. Med. Chem.*, 42, 210-212 (1999).

In addition, compounds of the present invention may be used in combination with therapeutic agents such as anti-resorptive agents; hormone replacement therapies; vitamin D and analogues thereof (e.g., 1,25-dihydroxy vitamin D3); elemental calcium and calcium supplements; cathepsin K inhibitors; MMP inhibitors; vitronectin receptor antagonists; Src $SH_2$ antagonists; Src kinase inhibitors; vacuolar $H^+$-AT- Pase inhibitors; PTH and its analogues and fragments; osteoprotegrin; Tibolone; p38 inhibitors; prostanoids; PPAR gamma antagonists or isoflavinoids (e.g., genistein, ipriflavone and testosterone).

The above other therapeutic agents, when employed in combination with the compounds of the present invention, may be used, for example, in those amounts indicated in the Physicians' Desk Reference (PDR) or as otherwise determined by one of ordinary skill in the art.

The compounds of the formula I can be administered for any of the uses described herein by any suitable means, for example, orally, such as in the form of tablets, capsules, granules or powders; sublingually; bucally; parenterally, such as by subcutaneous, intravenous, intramuscular, or intrastemal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compounds of formula I can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxypropyl cellulose (HPC), hydroxypropyl methyl cellulose (HPMC), sodium carboxymethyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Exemplary compositions for nasal, aerosol, or inhalation administration include solutions in saline which can contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for rectal administration include suppositories which can contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

The effective amount of a compound of the present invention can be determined by one of ordinary skill in the art, and includes exemplary dosage amounts for a adult human of from about 0.001 to 100 mg/kg of body weight of active compound per day, preferably 0.01 to 1 mg/kg of body weight of active compound per day, that can be administered in a single dose or in the form of individual divided doses, such as from 1 to 4 times per day. It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to NHR-associated conditions.

The following examples serve to better illustrate, but not limit, preferred embodiments of the invention.

EXAMPLES

The following abbreviations are employed in the Examples:
AcOEt=ethyl acetate
AcOH=acetic acid
aq.=aqueous
Ar=argon
Bn=benzyl
BOC=tert-butoxycarbonyl
BOP reagent=benzotriazol-1-yloxy-tris (dimethylamino) phosphonium hexafluorophosphate
br=broad
Bu=butyl
c=concentration
° C.=degrees Centigrade
CAN=ceric ammonium nitrate
CBZ=carbobenzyloxy or carbobenzoxy or benzyloxycarbonyl
$CDCl_3$=chloroform-d
$CD_3OD$=methanol-$d_4$
$CH_2Cl_2$=dichloromethane
$CHCl_3$=chloroform
$CH_3CN$=acetonitrile
$Cs_2CO_3$=cesium carbonate
d=day(s) or doublet
DBU=1,8-diazabicyclo[5.4.0]undec-7-ene
DEAD=diethylazodicarboxylate
DIAD=diisopropylazodicarboxylate
DIBAL=diisobutylaluminum hydride
DMAP=4-dimethylaminopyridine
DME=1,2-dimethoxyethane
DMF=dimethylformamide
DMSO=dimethylsulfoxide EDC=3-ethyl-3'-(dimethylamino)propylcarbodiimide hydrochloride
ES+=electrospray positive ionization
Et=ethyl
Et$_3$N=triethylamine
EtOAc=ethyl acetate
Et$_2$O=diethyl ether
EtOH=ethanol
FMOC=fluorenylmethoxycarbonyl
g=gram(s)
h=hour(s)
HCl=hydrochloric acid
hex=hexane or hexanes
HNO$_3$=nitric acid
H$_2$O=water
HOAc=acetic acid
HOAT=1-hydroxy-7-azabenzotriazole
HOBT=1-hydroxybenzotriazole hydrate
HPLC=high performance liquid chromatography
H$_3$PO$_4$=phosphoric acid
H$_2$SO$_4$=sulfuric acid
Hz=hertz
iPr=isopropyl
iPr$_2$NEt=diisopropylethylamine
iPrOH=isopropanol
K$_2$CO$_3$=potassium carbonate
KF=potassium fluoride
KHMDS=potassium bis(trimethylsilyl)amide
KHSO$_4$=potassium hydrogen sulfate
KOH=potassium hydroxide
KOTMS=potassium trimethylsilanolate
L=liter(s)
LAH=lithium aluminum hydride
LC/MS=high performance liquid chromatography/mass spectrometry
LiAlH$_4$=lithium aluminum hydride
LiHMDS=lithium bis(trimethylsilyl)amide
LiOH=lithium hydroxide
m=multiplet
M=molar
mCPBA=3-chloroperoxybenzoic acid
Me=methyl
MeOH=methanol
meq=milliequivalent(s)
mg=milligram(s)
MgCl$_2$=magnesium chloride
MgSO$_4$=magnesium sulfate
MHz=megahertz
µL=microliter(s)
min=minute(s)
mL=milliliter(s)
mm=millimeter(s)
mmol=millimole(s)
MnO$_2$=manganese dioxide
mol=mole(s)
mp=melting point
MS or Mass Spec=mass spectrometry
m/z=mass to charge ratio
N$_2$=nitrogen
NaBH$_4$=sodium borohydride
NaBH(OAc)$_3$=sodium triacetoxyborohydride
NaCNBH$_3$=sodium cyanoborohydride
NaHCO$_3$=sodium bicarbonate
NaHMDS=sodium bis(trimethylsilyl)amide
NaOH=sodium hydroxide
NaOEt=sodium ethoxide
NaOMe=sodium methoxide
NaSMe=sodium thiomethoxide
Na$_2$SO$_4$=sodium sulfate
nBuLi=n-butyllithium
NEt$_3$=triethylamine
NH$_4$Cl=ammonium chloride
NH$_4$OH=ammonium hydroxide
NMM=N-methylmorpholine
NMO=N-methylmorpholine N-oxide
NMP=N-methylpyrrolidinone
NMR=nuclear magnetic resonance
Pd/C=palladium on carbon
Pd(OAc)$_2$=Palladium acetate
Ph=phenyl
Ph$_3$P=triphenylphosphine
(Ph$_3$P)$_4$Pd=tetrakistriphenylphosphine palladium
P$_2$O$_5$=phosphorus pentoxide
POCl$_3$=phosphorus oxychloride
Pr=propyl
PtO$_2$=platinum oxide
PXPd$_2$=bis[di-tert-butylphosphinous chloride-κP]di-µ-chlorodipalladium
RT=room temperature
s=singlet
sat or sat'd=saturated
SOCl$_2$=thionyl chloride
t=triplet
TBS=tert-butyldimethylsilyl
tBu=tertiary butyl
TFA=trifluoroacetic acid
THF=tetrahydrofuran
Ti(OiPr)$_4$=titanium isopropoxide
TLC=thin layer chromatography
TMEDA=N,N,N',N'-tetramethylethylenediamine
TMS=trimethylsilyl or trimethylsilane
UV=ultraviolet HPLC analysis of the exemplified compounds was carried out under one of the following reverse phase methods, with the appropriate method and retention time noted in the Examples.

Method A: Phenomenex S5 ODS 4.6×50 mm column, gradient elution 0-100% B/A over 4 min (solvent A=10% MeOH/H$_2$O containing 0.1% H$_3$PO$_4$, solvent B=90% MeOH/H$_2$O containing 0.1% H$_3$PO$_4$), flow rate 4 mL/min, UV detection at 220 nm.

Method B: Phenomenex S5 ODS 4.6×50 mm column, gradient elution 0-50% B/A over 4 min (solvent A=10% MeOH/H$_2$O containing 0.1% H$_3$PO$_4$, solvent B=90% MeOH/H$_2$O containing 0.1% H$_3$PO$_4$), flow rate 4 mL/min, UV detection at 220 nm.

Method C: Phenomenex S5 ODS 4.6×50 mm column, gradient elution 0-100% B/A over 4 min (solvent A=10% MeOH/H$_2$O containing 0.1% TFA, solvent B=90% MeOH/H$_2$O containing 0.1% TFA), flow rate 4 mL/min, UV detection at 220 nm.

Method D: Zorbax S5 SB-C18 4.6×75 mm column, gradient elution 0-100% B/A over 8 min (solvent A=10% MeOH/H$_2$O containing 0.1% H$_3$PO$_4$, solvent B=90% MeOH/H$_2$O containing 0.1% H$_3$PO$_4$), flow rate 2.5 mL/min, UV detection at 220 nm.

Method E: Phenomenex S5 ODS 4.6×30 mm column, gradient elution 0-100% B/A over 2 min (solvent A=10% MeOH/H$_2$O containing 0.1% TFA, solvent B=90% MeOH/H$_2$O containing 0.1% TFA), flow rate 5 mL/min, UV detection at 220 nm.

Method F: YMC CombiScreen ODS 4.6×50 mm column, gradient elution 0-100% B/A over 4 min (solvent A=10%

MeOH/H$_2$O containing 0.1% H$_3$PO$_4$, solvent B=90% MeOH/H$_2$O containing 0.1% H$_3$PO$_4$), flow rate 4 mL/min, UV detection at 220 nm.

Example 1

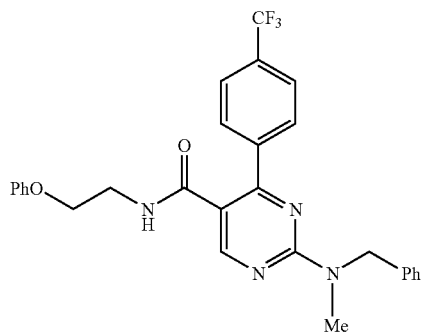

A.

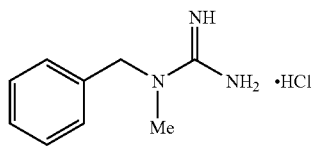

To a mixture of pyrazole-1-carboxyimidine (1.46 g, 10 mmol), benzylmethylamine (1.21 g, 10 mmol), and N,N-diisopropylethylamine (1.74 mL, 10 mmol) was added DMF (5 mL). The reaction mixture was stirred at room temperature overnight. Ether (50 mL) was added, and the product which became an oil was at the bottom of the flask. The mixture was sonicated and the top ether layer was decanted. This process was repeated several times until the product solidified. The solid was dried under high vacuum overnight to provide the title compound (2.0 g, 100%) as a white solid.

MS (ES+) m/z (M+H)$^+$=164.33. $^1$H NMR (400 MHz, CD$_3$OD): δ 2.91 (s, 3H), 4.51 (s, 2H), 7.24 (m, 5H). HPLC: Retention time=0.79 min (Method B).

B.

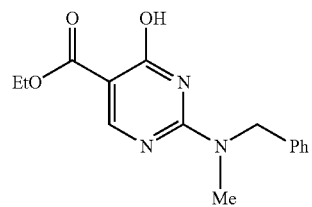

To a 100 mL Erlenmyer flask was added anhydrous EtOH (40 mL) and sodium metal (460 mg, 20 mmol) piece by piece. The mixture was stirred at room temperature for 20 minutes until no sodium was visible. The NaOEt solution was added to a flask containing the Part A compound (1.99 g, 10 mmol). To this suspension was added diethyl ethoxymethylenemalonate (4.04 mL, 20 mmol), upon which the suspension turned orange. The resulting mixture was heated at reflux overnight. Ethanol in the reaction was removed by rotary evaporation, and H$_2$O (30 mL) was added to the resulting mixture. A white precipitate formed after 30 min. Filtration gave the pyrimidine product as a yellow solid (2.1 g, 73%).

MS (ES+) m/z (M+H)$^+$=288.45. $^1$H NMR (400 MHz, CDCl$_3$): δ 1.39 (t, J=7.12 Hz, 3H), 3.17 (s, 3H), 4.38 (q, J=7.12 Hz, 2H), 4.95 (s, 2H), 8.70 (s, 1H). HPLC: Retention time=3.09 min (Method A).

C.

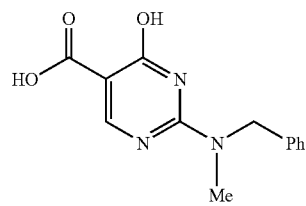

To a suspension of the Part B compound (1.93 g, 6.7 mmol) in EtOH (20 mL) was added a solution of KOH (1.13 g, 20.1 mmol) in EtOH (14 mL), and the resulting solution was heated at reflux overnight. A clear yellow solution formed. The reaction mixture was cooled to room temperature and a white precipitate formed. The solvent was removed in vacuo and the residue was treated with H$_2$O (30 mL), followed by 6N HCl (3 mL) upon which a precipitate formed. The mixture was chilled, and the solid was filtered and dried in a vacuum oven (50° C.) overnight to give the acid as a white solid (1.56 g, 90%).

MS (ES+) m/z (M+H)$^+$=260.43. $^1$H NMR (400 MHz, DMSO): δ 2.49 (s, 3H), 4.90 (s, 2H), 7.31 (m, 6H), 8.49 (br s, 1H). HPLC: Retention time=2.41 min (Method A).

D.

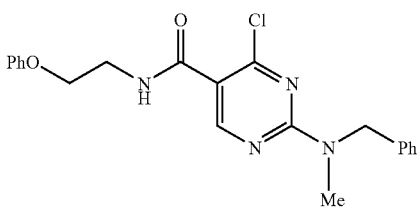

To a solution of POCl$_3$ (3.57 mL, 38.4 mmol) and the Part C compound (566 mg, 1.92 mmol) was added SOCl$_2$ (2.80 mL, 38.4 mmol). The suspension was heated at 110° C. overnight and a clear yellow solution formed. Following cooling to room temperature, the volatiles were removed and the yellow residue was dissolved in anhydrous THF (8.5 mL). The solution was cooled to −78° C., and NEt$_3$ (803 μL, 5.76 mmol) and 2-phenoxyethylamine (251 μL, 1.92 mmol) were added. The reaction mixture was stirred at −78° C. for 1.5 h. The solvent was removed in vacuo and the residue was purified by flash chromatography on silica gel eluting with a gradient of 0% to 50% EtOAc/hexane to give the chloropyrimidine as a sticky foam (560 mg, 73%).

MS (ES+) m/z (M+H)$^+$=397.46. $^1$H NMR (400 MHz, CDCl$_3$): δ 3.17 (s, 3H), 3.85-3.89 (m, 2H), 4.16 (t, J=5.28 Hz, 3H), 4.91 (d, J=13.16 Hz, 2H), 6.91-6.99 (m, 3H), 7.16-7.36 (m, 7H), 8.87 (b, 1H). HPLC: Retention time=3.81 min (Method A).

E.

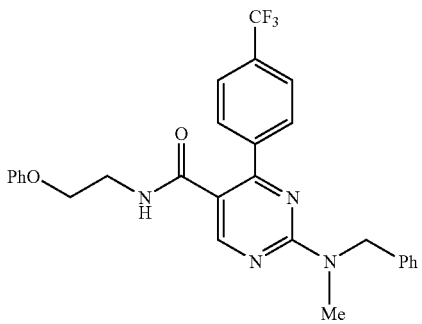

A mixture of the Part D compound (43 mg, 0.108 mmol), 4-(trifluoromethyl)benzeneboronic acid (31 mg, 0.162 mmol), K$_2$CO$_3$ (45 mg, 0.324 mmol), and PXPd$_2$ (2.2 mg, 0.003 mmol) in THF (0.5 mL) was heated at 100° C. overnight, then the reaction temperature was raised to 130° C. and heated further, again overnight; then, the reaction mixture was cooled to room temperature. The solvent was removed and the residue was purified by flash chromatography on silica gel, eluting with a gradient of 0% to 50% EtOAc/hexane to give a slightly yellow oil as a mixture, which was further purified by preparative HPLC (YMC S5 ODS 20×100 mm column; gradient elution 30-100% B/A over 15 min (solvent A=10% MeOH/H$_2$O containing 0.1% TFA, solvent B=90% MeOH/H$_2$O containing 0.1% TFA), flow rate 20 mL/min, UV detection at 220 nm) to give the title compound as a white solid (9 mg, 16%).

MS (ES+) m/z (M+H)$^+$=507.43. $^1$H NMR (400 MHz, CDCl$_3$): δ 3.22 (s, 3H), 3.66-3.70 (m, 2H), 3.94 (t, J=5.28 Hz, 2H), 4.97 (s, 2H), 5.89 (br s, 1H), 6.75 (d, J=8.8 Hz, 2H), 6.97 (t, J=7.48 Hz, 1H), 7.23-7.34 (m, 7H), 7.55 (d, J=7.48 Hz, 2H), 7.74 (br s, 2H), 8.70 (s, 1H). HPLC: Retention time=4.18 min (Method A).

Example 2

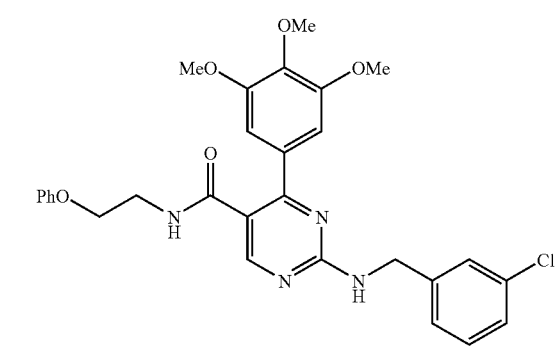

A.

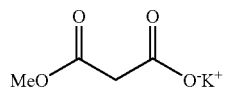

To a water-cooled solution of dimethylmalonate (132 g, 1 mol) in MeOH (500 mL) was added KOH (56 g, 1 mol) portionwise. The reaction mixture was stirred for 16 h, the solid was filtered off, and the filtrate was condensed to ~100 mL. Ether was added to precipitate out the solid, which was filtered and washed with ether, then dried to yield a white solid (102 g, 65%).

B.

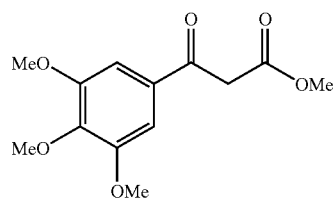

To a mixture of 3,4,5-trimethoxybenzoic acid (24.7 g, 116 mmol) and carbonyldiimidazole (20.8 g, 128 mmol) was added dry THF (300 mL) (Caution: gas evolution). The reaction mixture was stirred at room temperature for 4 h, then the Part A compound (20 g, 128 mmol) and MgCl$_2$ (12.2 g, 128 mmol) were added portionwise. The reaction mixture was stirred at 40° C. for 2 days. The resulting precipitate was removed by filtration, and the filtrate was diluted with water and acidified with 1N HCl until pH ~4. The mixture was extracted with ether (200 mL) and washed with water (2×100 mL), aq. NaHCO$_3$ and water, then dried over MgSO$_4$. Evaporation provided a crude product which was purified with flash chromatography on silica, eluting with a gradient of 0% to 50% EtOAc/hexane to give the beta-keto ester (18 g, 58%) as a white solid.

MS (ES+) m/z (M+Na)$^+$=291.22. $^1$H NMR (400 MHz, CDCl$_3$): δ 3.76 (s, 3H), 3.92 (s, 6H), 3.93 (S, 3H), 3.98 (s, 2H), 7.22 (s, 2H). HPLC: Retention time=2.26 min (Method C).

C.

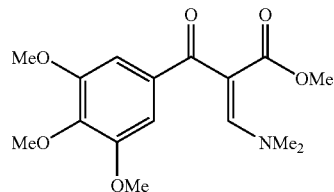

A mixture of the Part B compound (11.22 g, 42 mmol) and dimethylformamide dimethyl acetal (6.2 ml, 46 mmol) was heated at 90° C. for 2 h. The reaction mixture was cooled to room temperature then concentrated in vacuo to yield the vinylogous amide as a brown semi-solid, which was used directly in the next step without further purification.

MS (ES+) m/z (M+H)$^+$=324.29. HPLC: Retention time=2.08 min (Method C).

D.

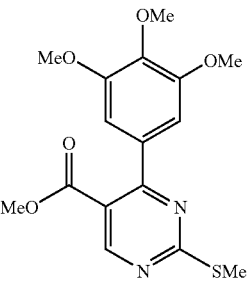

The Part C compound prepared above, 2-methyl-2-thiopseudourea (7 g, 25.2 mmol), and sodium acetate (8.6 g, 105 mmol) were combined in DMF (30 mL), and the mixture was heated at 80° C. for 16 h, then cooled to room temperature. Water was added resulting in a white slurry, which was extracted with CH$_2$Cl$_2$ (2×100 mL), dried over MgSO$_4$, and concentrated in vacuo. The crude product was purified by flash chromatography on silica gel, eluting with 1:2 EtOAc/hexane to give the pyrimidine (7.95 g, 54% for 2 steps) as a white solid.

MS (ES+) m/z (M+H)$^+$=351.22. $^1$H NMR (400 MHz, CDCl$_3$): δ 2.64 (s, 3H), 3.78 (s, 3H), 3.89 (s, 6H), 3.91 (S, 3H), 6.85 (s, 2H), 8.85 (s, 1H). HPLC: Retention time=3.17 min (Method C).

E.

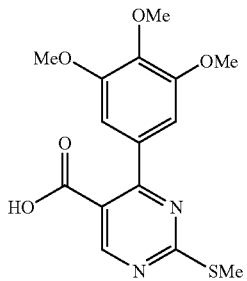

To a solution of the Part D compound (7.95 g, 22.7 mmol) in THF (50 ml) was added KOTMS (4.2 g, 90%, 29.5 mmol) in one portion, upon which the reaction solution turned yellow. After 14 h, the reaction mixture was partitioned between water and ether. The aqueous layer was acidified with 1N HCl to form a solid precipitate. The precipitate was filtered and washed with water. The solid residue was collected and dried in vacuo to provide the acid (6.95 g, 91%) as a pale yellow solid.

MS (ES+) m/z (M+H)$^+$=337.01. $^1$H NMR (400 MHz, CDCl$_3$): δ 2.65 (s, 3H), 3.89 (s, 6H), 3.91 (S, 3H), 6.88 (s, 2H), 8.99 (s, 1H).

HPLC: Retention time=1.95 min (Method C).

F.

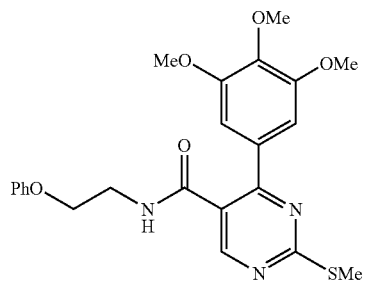

To a suspension of the Part E compound (4.57 g, 13.6 mmol) in CH$_2$Cl$_2$ (300 mL) was added NEt$_3$ (4 mL, 28.7 mmol) followed by addition of oxalyl chloride (7.8 mL, 2M in CH$_2$Cl$_2$, 15.6 mmol) and 5 drops of DMF (gas evolution). The clear reaction mixture was stirred at room temperature for 30 min, then partitioned between CH$_2$Cl$_2$ and water. The organic layer was dried over MgSO$_4$, concentrated in vacuo, then purified by flash chromatography on silica gel, eluting with 1:1 EtOAc/hexane to give the amide (3.63 g, 59%) as a white solid.

MS (ES+) m/z (M+H)$^+$=456.39. $^1$H NMR (400 MHz, CDCl$_3$): δ 2.63 (s, 3H), 3.68 (m, 2H), 3.83 (s, 3H), 3.85 (S, 6H), 3.95 (m, 2H), 5.95 (m, 1H), 6.74 (dd, J=8.8, 0.8 Hz, 2H), 6.95 (m, 1H), 6.97 (s, 2H), 7.23-7.27 (m, 2H), 8.77 (s, 1H). HPLC: Retention time 3.28 min (Method A).

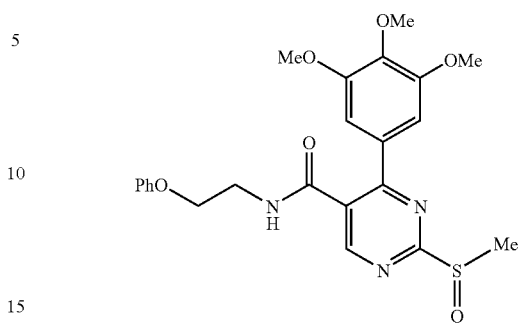

G.

To a solution of the Part F compound (3.63 g, 8.0 mmol) in dry CH$_2$Cl$_2$ (100 mL) at 0° C. was added 2-benzenesulfonyl-3-phenyl-oxaziridine (2.3 g, 8.8 mmol) and the reaction mixture was stirred at room temperature for 16 h. The reaction mixture was then concentrated in vacuo, and the crude product was purified by flash chromatography on silica gel, eluting with EtOAc to yield the sulfoxide (3.2 g, 80%) as a white solid.

$^1$H NMR (400 MHz, CDCl$_3$): δ 2.96 (s, 3H), 3.75 (m, 2H), 3.84 (s, 3H), 3.86 (S, 6H), 4.00 (dd, J=8.7, 4.3 Hz, 2H), 6.44 (m, 1H), 6.76 (dd, J=8.7, 0.8 Hz, 2H), 6.96 (t, J=7.6 Hz, 1H), 7.08 (s, 2H), 7.08-7.28 (m, 2H), 8.98 (s, 1H). HPLC: Retention time=2.77 min (Method A).

H.

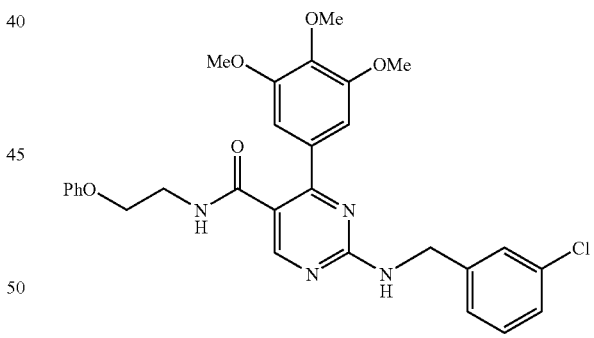

A mixture of m-chlorobenzylamine (23.5 mL, 0.19 mmol) and the Part G compound (75.4 mg, 0.16 mmol) in THF (4 mL) was heated at 60° C. for 16 h, then cooled to room temperature. The solvent was removed and the crude product was purified by flash chromatography on silica gel eluting with 50% EtOAc/hexane to give the title compound (71 mg, 70%) as a white solid.

MS (ES+) m/z (M+H)$^+$=549.33. $^1$H NMR (400 MHz, CDCl$_3$): δ 3.61-3.65 (m, 2H), 3.78 (s, 6H), 3.80 (s, 3H), 3.91 (t, J=5.0 Hz, 2H), 4.61 (d, J=4.2 Hz 2H), 5.94 (br s, 1H), 6.73-6.75 (m, 2H), 6.82 (s, 2H), 6.93 (t, J=7.36 Hz, 1H), 7.18-7.27 (m, 6H), 7.32 (s, 1H), 8.59 (br s, 1H). HPLC: Retention time=3.71 min (Method A).

Example 3

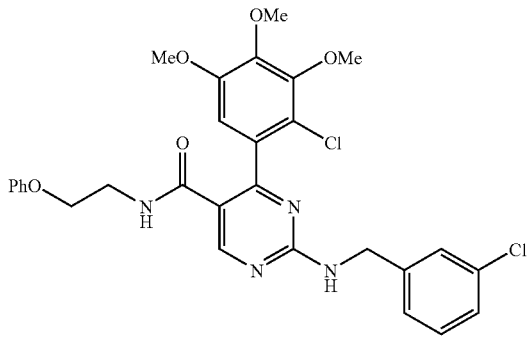

A.

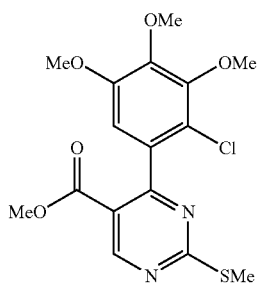

A solution of the Example 2 Part D compound (0.350 g, 1.0 mmol) and N-chlorosuccinimide (0.134 g, 1.0 mmol) in chloroform (2 mL) was stirred at 80° C. for 3 h. The reaction was cooled to room temperature and the excess solvent was removed in vacuo. Column chromatography on silica gel (0% to 50% ethyl acetate in hexane) gave 0.293 g of the aryl chloride as a white solid.

$^1$H NMR (400 MHz, CDCl$_3$): δ 9.05 (s, 1H), 6.76 (s, 1H), 3.95 (s, 3H), 3.92 (s, 3H), 3.89 (s, 3H), 3.76 (s, 3H), 2.63 (s, 3H). HRMS m/z Calc'd. for C$_{16}$H$_{18}$N$_2$O$_5$SCl [M+H]$^+$: 385.0625. Found 385.0635. HPLC: Retention time=3.25 min (Method F).

B.

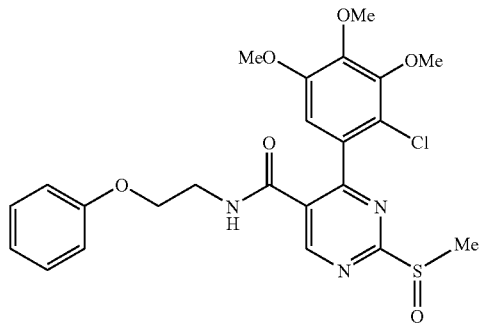

To a clear, colorless solution of the Part A compound (0.280 g, 0.73 mmol) in THF (2.4 mL) was added KOTMS (0.135 g, 0.95 mmol). The resulting yellow solution was stirred at room temperature for 24 h. The reaction was diluted with water (10 mL) and extracted with diethyl ether (2×10 mL). The aqueous layer was acidified with 1 M HCl. The resulting cloudy mixture was extracted with methylene chloride (2×10 mL). The combined organic layers were washed with brine (10 mL), dried over Na$_2$SO$_4$, filtered, and concentrated to give 0.233 g of the carboxylic acid, as a white solid of the structure

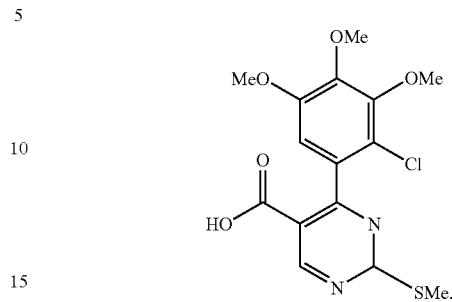

$^1$H NMR (400 MHz, DMSO-d$_6$): δ 13.2 (s, 1H), 8.97 (s, 1H), 6.86 (s, 1H), 3.77-3.68 (m, 9H), 2.49 (s, 3H). HRMS m/z Calc'd. for C$_{15}$H$_{14}$N$_2$O$_5$SCl [M−H]$^-$: 369.0312. Found 369.0316. HPLC: Retention time=3.00 min (Method F)

A mixture of the carboxylic acid (0.220 g, 0.59 mmol) and thionyl chloride (0.87 mL, 11.9 mmol) was stirred at 90° C. for 2 h. Upon cooling to room temperature, excess thionyl chloride was removed in vacuo. The residue was dissolved in THF (2 mL) and cooled to −78° C. Next, triethylamine (0.25 mL, 1.78 mmol) and 2-phenoxyethylamine (0.16 mL, 1.19 mmol) was added. After 2 h, the reaction was warmed to room temperature. Water (5 mL) was added and the reaction was extracted with ethyl acetate (10 mL). The organic layer was washed with brine (10 mL), dried over Na$_2$SO$_4$, filtered and concentrated. Column chromatography on silica gel (0% to 50% ethyl acetate in hexane) gave 0.235 g of the amide as a white solid of the structure

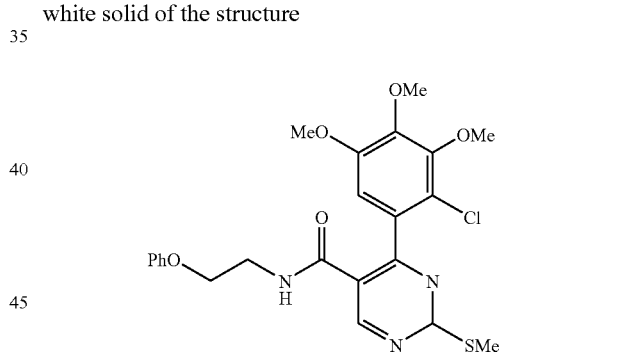

$^1$H NMR (400 MHz, CDCl$_3$): δ 8.98 (s, 1H), 7.28-7.24 (m, 2H), 6.99-6.94 (m, 1H), 6.78-6.76 (m, 3H), 6.03 (t, J=5.3, 1H), 3.92-3.88 (m, 2H), 3.83 (s, 6H), 3.82 (s, 3H), 3.65 (q, J=5.3 Hz, 2H), 2.61 (s, 3H). HRMS m/z Calc'd. for C$_{23}$H$_{23}$N$_3$O$_5$SCl [M−H]$^-$: 488.1047. Found 488.1028. HPLC: Retention time=3.34 min (Method F).

To a clear, colorless, solution of the amide (0.225 g, 0.46 mmol) in methylene chloride (4 mL) was added 2-benzenesulfonyl-3-phenyl-oxaziridine (0.132 g, 0.51 mmol). The resulting yellow solution was stirred at room temperature for 26 h. The reaction was concentrated and column chromatography on silica gel (0% to 100% ethyl acetate in hexane) gave 0.150 g (30% over 4 steps) of the sulfoxide as a white solid.

$^1$H NMR (400 MHz, CDCl$_3$): δ 9.26 (s, 1H), 7.27 (t, J=7.5 Hz, 2H), 6.96 (t, J=7.5 Hz, 1H), 6.82 (s, 1H), 6.78 (d, J=7.5 Hz, 2H), 6.38 (t, J=5.3 Hz, 1H), 3.94 (t, J=5.3 Hz, 2H), 3.84 (s, 9H), 3.70 (q, J=5.3 Hz, 2H), 2.99 (s, 3H). HRMS m/z Calc'd. for C$_{23}$H$_{25}$N$_3$O$_6$SCl [M+H]$^+$: 506.1153. Found 506.1133. HPLC: Retention time=2.90 min (Method F)

C.

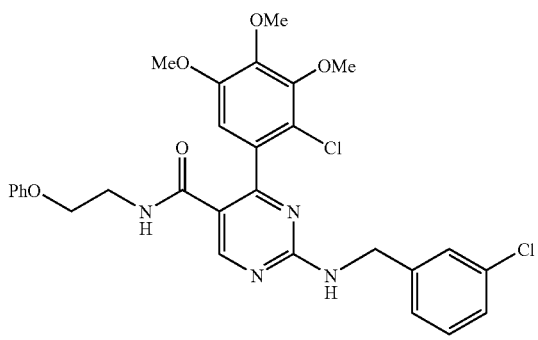

To a sealed tube (with a teflon sealed cap) was added the Part B sulfoxide (0.040 g, 0.079 mmol), m-chlorobenzylamine (0.0224 g, 0.158 mmol), and THF (1 mL). The reaction was stirred at 80° C. for 18 h. The reaction was cooled to room temperature and concentrated. Column chromatography on silica gel (0% to 100% ethyl acetate in hexane) gave 0.041 g of the crude product as an off-white gum. Preparative HPLC (YMC S5 ODS 20×200 mm column, gradient elution 40-100% B/A over 20 min (solvent A=10% MeOH/H$_2$O containing 0.1% TFA, solvent B=90% MeOH/H$_2$O containing 0.1% TFA), flow rate 20 mL/min, UV detection at 220 nm) gave a yellow gum. The yellow gum was dissolved in methylene chloride (5 mL), washed with saturated NaHCO$_3$ (5 mL), brine (5 mL), dried over Na$_2$SO$_4$, filtered and concentrated to give 0.022 g (48%) of the title compound as a white solid.

$^1$H NMR (400 MHz, DMSO-d$_6$, 80° C.): δ 8.58 (s, 1H), 8.07 (s, 1H), 7.84 (s, 1H), 7.38-7.25 (m, 6H), 6.95-6.88 (m, 3H)1, 6.77 (s, 1H), 4.60-4.53 (m, 2H), 3.96-3.90 (m, 2H), 3.76 (s, 3H), 3.79 (s, 3H), 3.81 (s, 3H), 3.46-3.40 (m, 2H). HRMS m/z Calc'd. for C$_{29}$H$_{29}$N$_4$O$_5$Cl$_2$ [M+H]$^+$: 583.1515. Found 583.1514. HPLC: Retention time=7.67 min (Method D)

Example 4

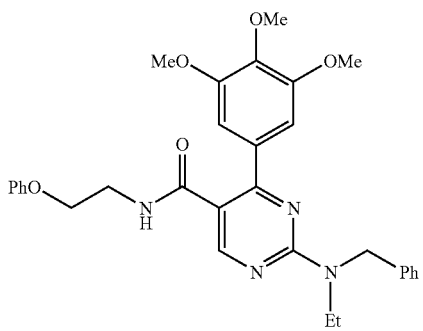

A.

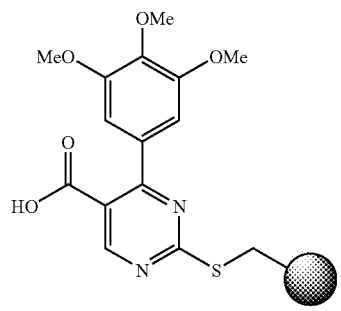

Merrifield resin (35 g, ~56 mmol) was swollen with DMF (350 mL) followed by addition of thiourea (21.3 g, 280 mmol). The mixture was agitated on an orbital shaker at 75° C. for 3 d, cooled to room temperature, and filtered. The resulting solid was washed with DMF (3×300 mL), THF (3×300 mL), and CH$_2$Cl$_2$ (3×300 mL), then dried in vacuo to provide the desired resin as a white solid.

B.

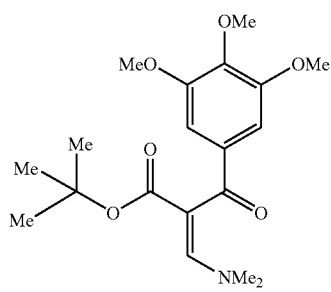

The Part B compound was prepared according to the procedure for preparation of the Example 50 Part B compound.

C.

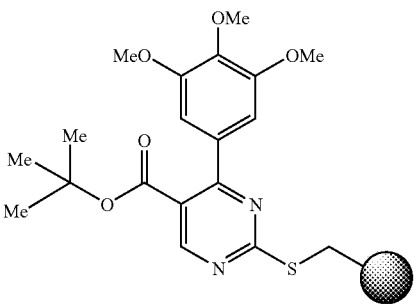

The Part A resin (5.0 g, 9 mmol) was swollen in DMF (50 mL) followed by addition of the Part B compound (8.20 g, 24 mmol) and N,N-diisopropylethylamine (7.9 mL). The reaction mixture was degassed then agitated at room temperature for 3 d, filtered, washed with DMF (3×55 mL), MeOH (3×55 mL), and CH$_2$Cl$_2$ (3×55 mL), then dried in vacuo to provide the product resin as a white solid.

The resin structure was confirmed by mCPBA oxidation followed by cleavage with excess pyrrolidine, resulting in the expected pyrrolidinylpyrimidine product.

MS (ES+) m/z (M+H)$^+$=415. HPLC: Retention time=1.93 min (Method E).

D.

A mixture of the Part C compound (15 g) in 1:1 TFA/1,2-dichloroethane (150 mL) was degassed then agitated at room temperature overnight, filtered, washed with THF (3×100 mL), MeOH (3×100 mL), and CH$_2$Cl$_2$ (3×100 mL), then dried in vacuo to provide the product resin as a white solid.

The resin structure was confirmed by mCPBA oxidation followed by cleavage with excess pyrrolidine, resulting in the expected product.

MS (ES+) m/z (M+H)$^+$=359. HPLC: Retention time=1.54 min (Method E).

E.

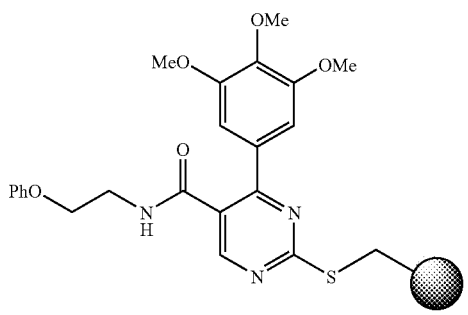

A set of Irori MicroKans containing RF tags were filled with the Part D resin (25 mg/Kan) and placed in a reservoir containing EDC (0.25M), HOBt (0.125M), and N,N-diisopropylethylamine (0.5M) in NMP (1 mL/Kan). The mixture was degassed and shaken for 30 min, then 2-phenoxyethylamine (0.25M) was added. The set of MicroKans were shaken for 2 d at room temperature, filtered, washed with DMF (3×), THF (3×), and CH$_2$Cl$_2$ (3×), then dried in vacuo to provide the product resin as a white solid.

F.

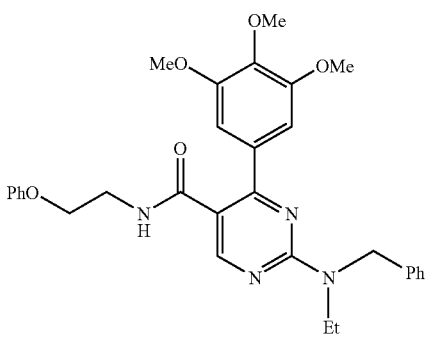

One of the MicroKans from Part E was placed in a reservoir containing CH$_2$Cl$_2$ (1 mL). The mixture was degassed and mCPBA (10 eq) was added. The reaction mixture was shaken at room temperature overnight, filtered, washed with DMF (3×), THF (3×), and CH$_2$Cl$_2$ (3×), then dried in vacuo. The resulting MicroKan was placed in a reservoir containing N-ethylbenzylamine (1.5 mL of a 0.25M solution in CH$_3$CN), degassed, then heated at 70° C. for 2 d. The reaction mixture was filtered, and the filtrate was concentrated to provide the crude product, which was purified by preparative reverse phase HPLC (Shimadzu VP-ODS 20×50 mm column, gradient elution 25-100% B/A over 6.5 min and 100% B over 3 min (solvent A=10% MeOH/H$_2$O containing 0.1% TFA, solvent B=90% MeOH/H$_2$O containing 0.1% TFA), flow rate 20 mL/min, UV detection at 220 nm and MS detection) to give the title compound (1.1 mg, 11% for 3 steps).

MS (ES+) m/z (M+H)$^+$=543.0. HPLC: Retention time=1.98 min (Method E).

Examples 5 to 49

Examples 5 to 49 set out in Table 1 were prepared according to the general procedures described in Example 2 and Example 4.

TABLE 1

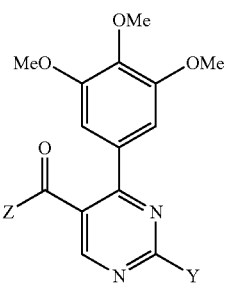

| Example No. | Z | Y | [M + H]$^+$ | HPLC R$_t$ (min) [Method] |
|---|---|---|---|---|
| 5 | 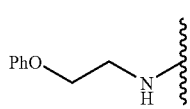 |  | 559.0 | 1.80 [E] |

TABLE 1-continued

| Example No. | Z | Y | [M + H]+ | HPLC R$_t$ (min) [Method] |
|---|---|---|---|---|
| 6 | PhO-CH$_2$CH$_2$-NH- | -NH-CH(CH$_2$OH)-CH$_2$-C$_6$H$_4$-Me (p) | 571.2 | 3.52 [C] |
| 7 | PhO-CH$_2$CH$_2$-NH- | -NH-CH(Me)-(3,4-methylenedioxyphenyl) | 572.2 | 7.27 [D] |
| 8 | PhO-CH$_2$CH$_2$-NH- | -NH-CH(Ph)-CH$_2$-Me | 542.4 | 3.75 [C] |
| 9 | PhO-CH$_2$CH$_2$-NH- | -NH-CH(CH$_2$OH)-CH$_2$-C$_6$H$_4$-F (p) | 576.2 | 6.90 [D] |
| 10 | PhO-CH$_2$CH$_2$-NH- | -NH-CH(CH$_2$OH)-CH$_2$-cyclohexyl | 565.1 | 1.96 [E] |
| 11 | PhO-CH$_2$CH$_2$-NH- | -NH-CH$_2$CH$_2$-Ph | 528.2 | 7.16 [D] |
| 12 | PhO-CH$_2$CH$_2$-NH- | -NH-CH$_2$-C$_6$H$_4$-OMe (m) | 543.2 | 3.51 [C] |

TABLE 1-continued
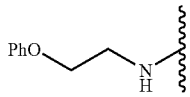
| Example No. | Z | Y | [M + H]⁺ | HPLC R$_t$ (min) [Method] |
|---|---|---|---|---|
| 13 | 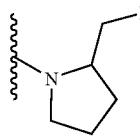 | 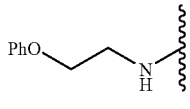 | 568.1 | 3.57 [C] |
| 14 | 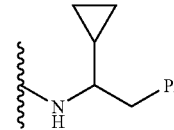 | 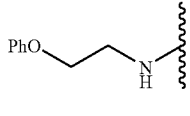 | 568.2 | 7.91 [D] |
| 15 | 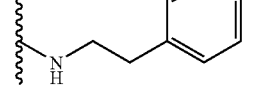 | 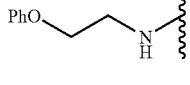 | 546.3 | 3.57 [C] |
| 16 | 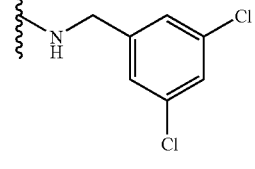 | 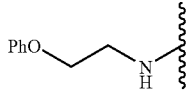 | 582.3 | 3.90 [C] |
| 17 | 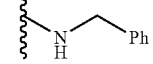 | 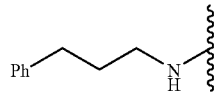 | 515.2 | 1.79 [E] |
| 18 | 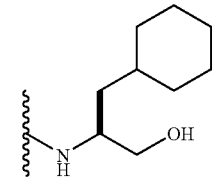 | 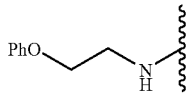 | 563.1 | 1.95 [E] |
| 19 | 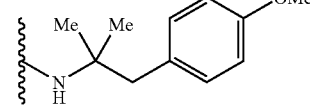 | 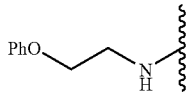 | 586.2 | 3.87 [C] |
| 20 | 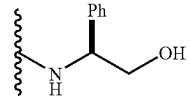 | | 544.2 | 3.26 [C] |

TABLE 1-continued

[Core structure: 4-(3,4,5-trimethoxyphenyl)pyrimidine with 5-C(=O)-Z and 2-Y substituents]

| Example No. | Z | Y | [M + H]+ | HPLC R_t (min) [Method] |
|---|---|---|---|---|
| 21 | PhO-CH2CH2-NH- | (2R)-1,2,3,4-tetrahydronaphthalen-2-ylamino | 554.4 | 3.54 [C] |
| 22 | PhO-CH2CH2-NH- | N-benzyl-N-(2-hydroxyethyl)amino | 558.2 | 7.22 [D] |
| 23 | PhO-CH2CH2-NH- | 2-benzylpiperidin-1-yl | 582.3 | 8.32 [D] |
| 24 | PhO-CH2CH2-NH- | (2S)-2-amino-4-methyl-1-pentanol-NH- | 525.4 | 3.41 [A] |
| 25 | PhO-CH2CH2-NH- | (thiophen-2-ylmethyl)amino | 520.3 | 3.42 [C] |
| 26 | PhO-CH2CH2-NH- | 2-(N-ethyl-N-(3-methylphenyl)amino)ethylamino | 586.2 | 1.57 [E] |
| 27 | Ph-(CH2)4-NH- | (1,3-benzodioxol-5-ylmethyl)amino | 571.0 | 1.91 [E] |
| 28 | PhO-CH2CH2-NH- | (3-methylbutyl)amino | 495.3 | 1.87 [E] |

TABLE 1-continued

| Example No. | Z | Y | [M + H]⁺ | HPLC $R_t$ (min) [Method] |
|---|---|---|---|---|
| 29 | Ph(CH₂)₃NH– | –NH–CH₂–(benzo[1,3]dioxol-5-yl) | 557.0 | 1.83 [E] |
| 30 | PhOCH₂CH₂NH– | –NH–CH(CH₂Ph)–CO₂Me | 586.2 | 3.52 [C] |
| 31 | PhOCH₂CH₂NH– | –NH–CH₂–(3-SMe-C₆H₄) | 560.3 | 3.32 [C] |
| 32 | PhOCH₂CH₂NH– | –NH–(indan-2-yl) | 541.2 | 1.93 [E] |
| 33 | PhOCH₂CH₂NH– | –NH–CH(Me)–CH₂Ph | 543.2 | 2.05 [E] |
| 34 | Ph(CH₂)₄NH– | –N(Et)–CH₂Ph | 555.3 | 2.12 [E] |
| 35 | PhOCH₂CH₂NH– | –NH–CH₂–(5-Me-furan-2-yl) | 518.3 | 3.42 [C] |
| 36 | (4-Cl-C₆H₄)–CH₂–CH(Me)–NH– | –NH–CH(CH₂-cyclohexyl)–CH₂OH | 597.0 | 1.91 [E] |

TABLE 1-continued
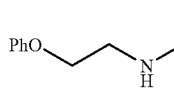
| Example No. | Z | Y | [M + H]⁺ | HPLC R$_t$ (min) [Method] |
|---|---|---|---|---|
| 37 | 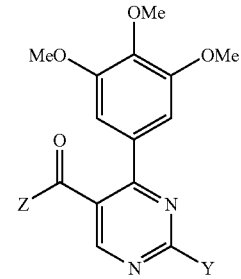 | 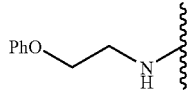 | 495.4 | 1.83 [E] |
| 38 | 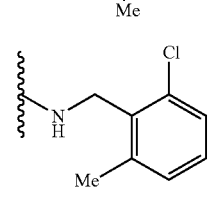 | 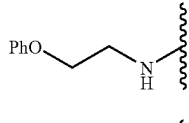 | 563.2 | 1.96 [E] |
| 39 | 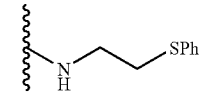 | 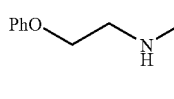 | 561.1 | 1.90 [E] |
| 40 | 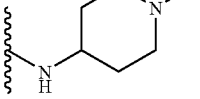 | 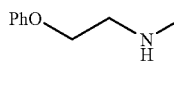 | 580.0 | 1.74 [E] |
| 41 | 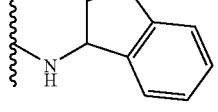 | 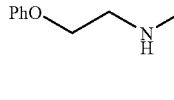 | 541.3 | 3.69 [C] |
| 42 | 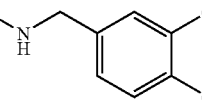 | 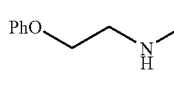 | 561.3 | 1.58 [E] |
| 43 | 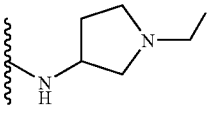 | 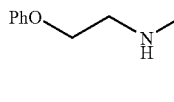 | 584.4 | 1.52 [E] |
| 44 | 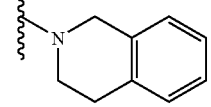 | 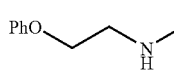 | 541.2 | 2.05 [E] |
| 45 | 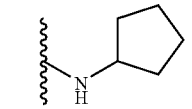 | | 493.3 | 1.80 [E] |

TABLE 1-continued

| Example No. | Z | Y | [M + H]+ | HPLC Rt (min) [Method] |
|---|---|---|---|---|
| 46 | PhO-CH2CH2-NH- | -NH-CH2-C6H4-NMe2 (4-) | 557.2 | 5.33 [D] |
| 47 | PhO-CH2CH2-NH- | -NH-CH(Me)-Ph | 528.2 | 3.53 [C] |
| 48 | PhO-CH2CH2-NH- | -NH-CH(Me)-C6H4-CF3 (3-) | 597.4 | 3.73 [C] |
| 49 | PhO-CH2CH2-NH- | -NH-CH2-C6H4-OCF3 (3-) | 598.3 | 3.73 [C] |

Example 50

A.

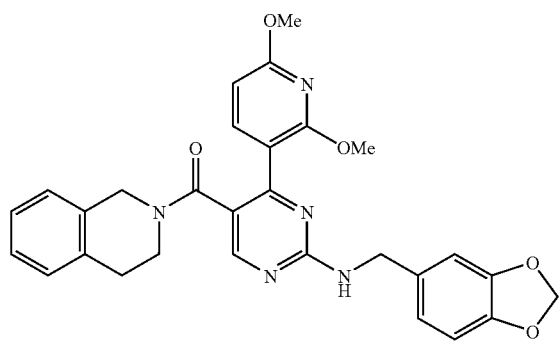

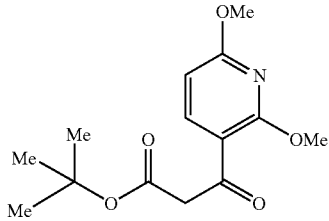

To a solution of 2,6-dimethoxynicotinic acid (18.9 g, 100 mmol) in THF (100 mL) was added 1,1'carbonyldiimidazole (17.9 g, 110 mmol) and the reaction mixture was stirred at room temperature overnight. A solution of tert-butyl acetate (40.4 mL, 300 mmol) in THF (200 mL) was added, and the reaction mixture was cooled to −78° C. A solution of lithium bis(trimethylsilyl)amide in THF (360 mL, 1.0M, 360 mmol) was added dropwise over 40 min. During addition, a white precipitate began to form. Following addition, the thick off-white slurry was mechanically stirred for 2 h, then poured onto crushed ice (300 g). The resulting mixture was acidified to pH 4.5 then extracted with ether (4×300 mL). The combined organic extracts were washed with brine, dried over MgSO$_4$, then concentrated in vacuo to provide the beta-keto ester (22 g) as a pale yellow oil, which was utilized without further purification.

B.

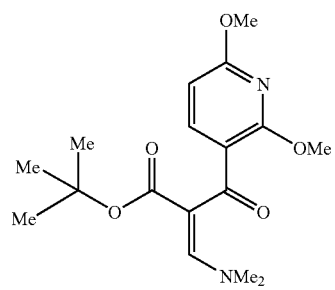

A mixture of the Part A compound (22 g) and dimethylformamide dimethyl acetal (10.5 mL, 79 mmol) in toluene (100 mL) was heated at reflux for 2 h, cooled to room temperature, and concentrated in vacuo to give a pale yellow residue. The crude product was purified by flash chromatography on silica gel, eluting with a step gradient of 5% to 50% EtOAc/hexane to give the title compound (22.3 g, 67% for two steps) as a yellow solid.

MS (ES+) m/z (M+H)$^+$=359.03. $^1$H NMR (500 MHz, CDCl$_3$): δ 1.13 (s, 9H), 1.80 (s, 3H), 2.90 (s, 9H), 3.85 (d, 6H), 6.25 (d, 1H), 7.63 (s, 1H), 7.74 (d, 1H). HPLC: Retention time=1.67 min (Method E).

C.

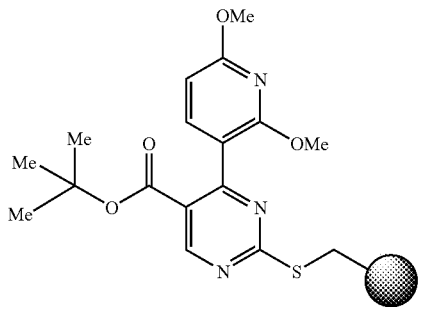

The Part A resin (12.5 g, 20 mmol) was swollen in DMF (120 mL) followed by addition of the Part B compound (17.0 g, 50 mmol) and N,N-diisopropylethylamine (17.5 mL, 100 mmol). The reaction mixture was degassed and agitated at room temperature for 3 d, filtered, washed with DMF (3×100 mL), MeOH (3×100 mL), and CH$_2$Cl$_2$ (3×100 mL), then dried in vacuo to provide the product resin as a white solid.

The resin structure was confirmed by mCPBA oxidation followed by cleavage with excess pyrrolidine, resulting in the expected pyrrolidinylpyrimidine product.

MS (ES+) m/z (M+H)$^+$=376. HPLC: Retention time=2.03 min (Method E).

D.

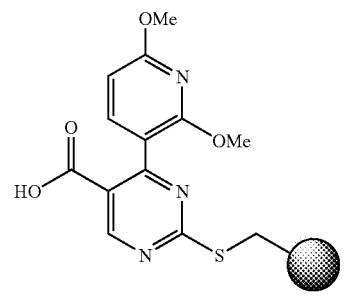

A mixture of the Part C compound (15 g) in 1:1 TFA/1,2-dichloroethane (150 mL) was degassed and agitated at room temperature overnight, filtered, washed with THF (2×100 mL), MeOH (2×100 mL), and CH$_2$Cl$_2$ (4×100 mL), then dried in vacuo to provide the product resin as a white solid.

The resin structure was confirmed by mCPBA oxidation followed by cleavage with excess pyrrolidine, resulting in the expected product.

MS (ES+) m/z (M+H)$^+$=330. HPLC: Retention time=1.62 min (Method E).

E.

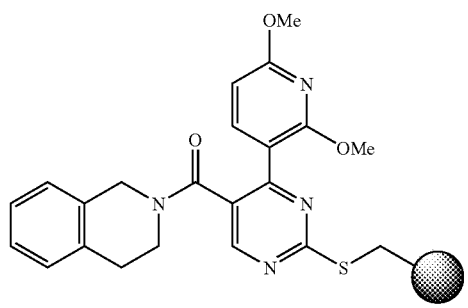

To a mixture of the Part D resin (100 mg, ~0.1 mmol) in NMP (1 mL) was added EDC (48 mg, 0.25 mmol), HOBt (17 mg, 0.125 mmol), and N,N-diisopropylethylamine (87 μL, 0.50 mmol). The mixture was degassed and shaken for 30 min, then 1,2,3,4-tetrahydroisoquinoline (33 mg, 0.25 mmol) was added. The reaction mixture was stirred at room temperature for 2 d, filtered, washed with DMF (3×1 mL), THF (3×1 mL), and CH$_2$Cl$_2$ (3×1 mL), and dried in vacuo to give a light brown solid, which was utilized without further purification.

F.

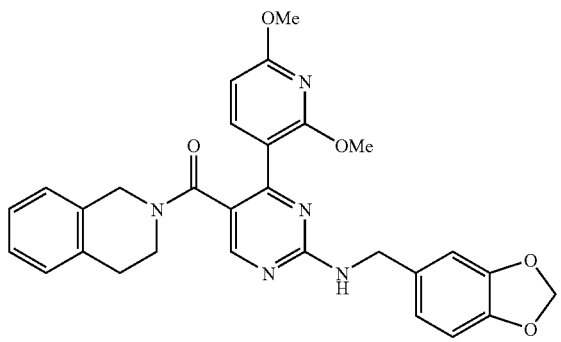

The Part E resin above and mCPBA (170 mg, 1.0 mmol) were combined in $CH_2Cl_2$ (1 mL). The reaction mixture was degassed then shaken at room temperature overnight, filtered, then washed with DMF (3×), THF (3×), and $CH_2Cl_2$ (3×). To this wet resin was added a solution of piperonylamine in $CH_3CN$ (1.5 mL, 0.25M), and the mixture was degassed, then heated at 70° C. for 2 d. The reaction mixture was filtered, and the filtrate was concentrated to provide the crude product, which was purified by preparative reverse phase HPLC (Shimadzu VP-ODS 20×50 mm column, gradient elution 25-100% B/A over 6.5 min and 100% B over 3 min (solvent A=10% $MeOH/H_2O$ containing 0.1% TFA, solvent B=90% $MeOH/H_2O$ containing 0.1% TFA), flow rate 20 mL/min, UV detection at 220 nm and MS detection) to give the product TFA salt. The resulting salt was free based to provide the title compound (8 mg, 15%) as a light brown solid.

MS (ES+) m/z $(M+H)^+$=526.0. $^1H$ NMR (500 MHz, $CDCl_3$): δ 3.44 (s, 6H), 3.48 (s, 2H), 3.81 (s, 4H), 3.87 (s, 2H), 4.48 (s, 1H), 4.57 (d, J=6.0 Hz, 2H), 5.92 (s, 2H), 6.34 (dd, J=8.2 Hz, 1H), 6.75 (m, 3H), 7.13 (m, 3H), 7.80 (dd, J=7.7 Hz, 1H). HPLC: Retention time=1.98 min (Method E).

Examples 51 to 71

Examples 51 to 71 set out in Table 2 were prepared according to the general procedure described in Example 50.

TABLE 2

| Example No. | Z | Y | [M + H]+ | HPLC R_t (min) [Method] |
|---|---|---|---|---|
| 51 | PhO-CH2CH2-NH- | piperonylamine-NH- | 530.0 | 1.93 [E] |
| 52 | Ph-(CH2)3-NH- | piperonylamine-NH- | 528.0 | 1.97 [E] |
| 53 | 4-Cl-C6H4-CH2-CH(Me)-NH- | piperonylamine-NH- | 562.0 | 2.04 [E] |
| 54 | Ph-(CH2)4-NH- | piperonylamine-NH- | 542.1 | 2.05 [E] |

TABLE 2-continued
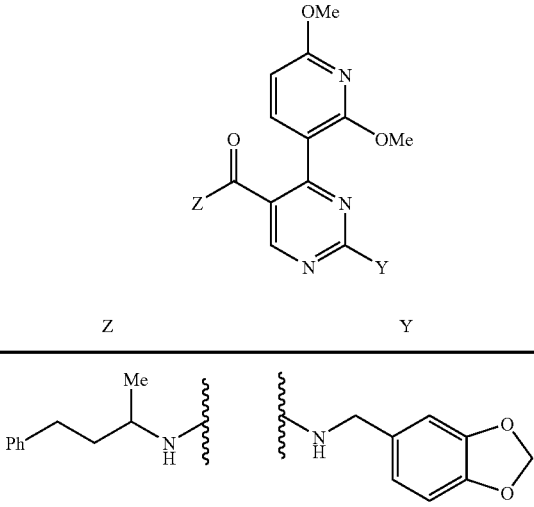
| Example No. | Z | Y | [M + H]⁺ | HPLC R$_t$ (min) [Method] |
|---|---|---|---|---|
| 55 | 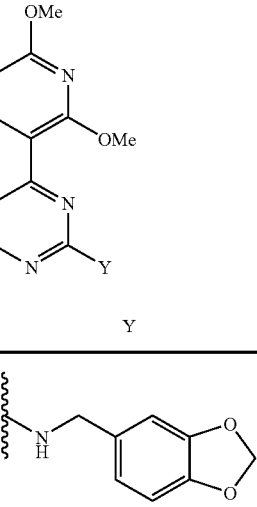 | 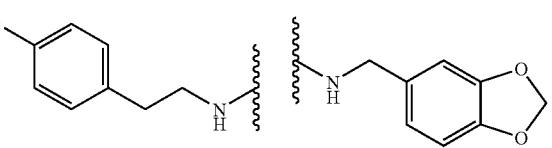 | 542.1 | 2.10 [E] |
| 56 | 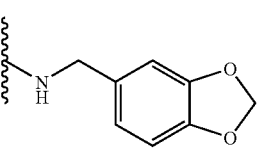 | 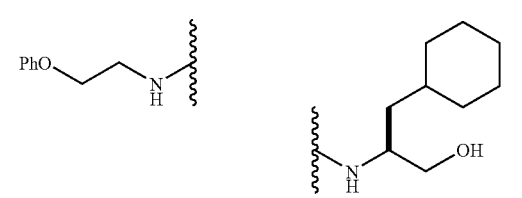 | 564.1 | 2.03 [E] |
| 57 | 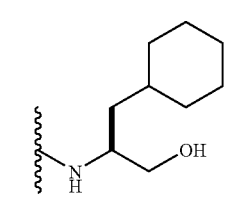 | 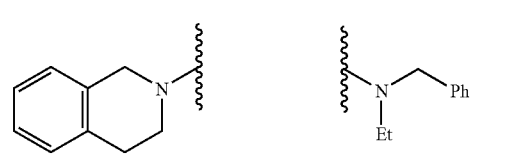 | 536.6 | 2.06 [E] |
| 58 | 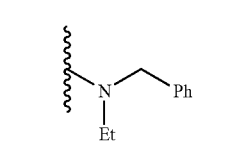 | 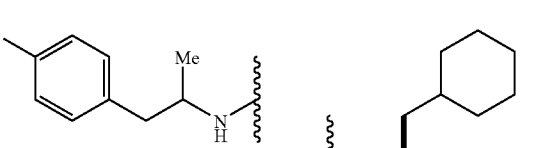 | 510.1 | 2.25 [E] |
| 59 | 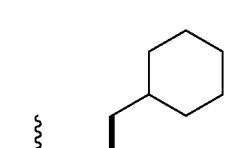 | 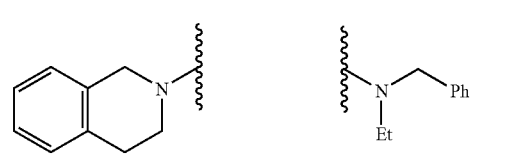 | 568.6 | 2.15 [E] |
| 60 | 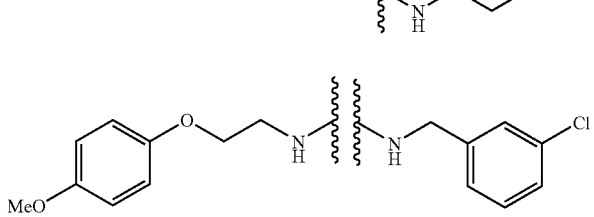 | 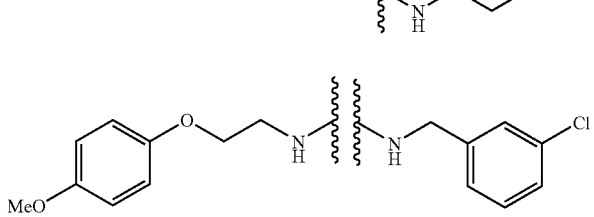 | 550.4 | 1.99 [E] |
| 61 | 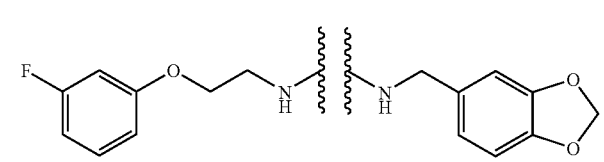 | 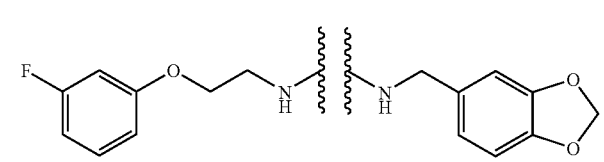 | 548.4 | 1.94 [E] |

TABLE 2-continued
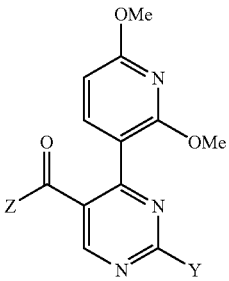
| Example No. | Z | Y | [M + H]+ | HPLC Rt (min) [Method] |
|---|---|---|---|---|
| 62 |  | 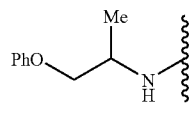 | 544.4 | 1.97 [E] |
| 63 | 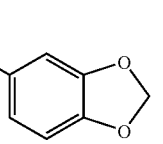 | 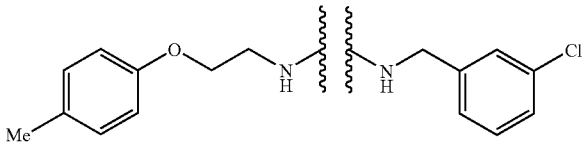 | 534.4 | 2.08 [E] |
| 64 |  | 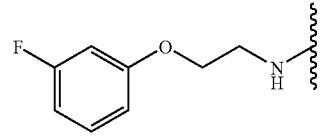 | 537.0 | 2.04 [E] |
| 65 | 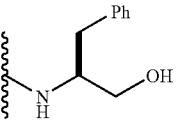 | 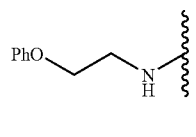 | 562.5 | 2.02 [E] |
| 66 | 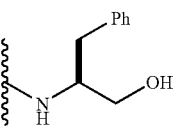 | 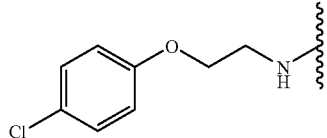 | 530.5 | 1.88 [E] |
| 67 | 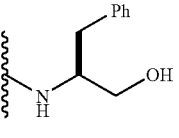 | 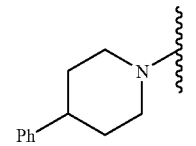 | 564.4 | 1.97 [E] |
| 68 | 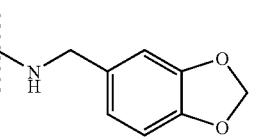 | 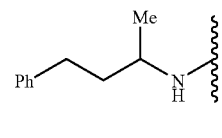 | 554.4 | 2.09 [E] |
| 69 | 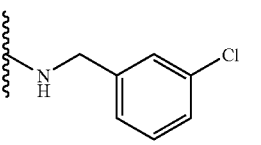 | | 533.0 | 2.08 [E] |

TABLE 2-continued

| Example No. | Z | Y | [M + H]+ | HPLC R$_t$ (min) [Method] |
|---|---|---|---|---|
| 70 | HO-C$_6$H$_4$-CH$_2$-CH(Me)-NH- | -NH-CH$_2$-C$_6$H$_4$-Cl (3-Cl) | 535.0 | 1.89 [E] |
| 71 | F-C$_6$H$_4$-CH$_2$-C(Me)$_2$-NH- | -NH-CH$_2$-C$_6$H$_4$-Cl (3-Cl) | 550.4 | 2.09 [E] |

Example 72

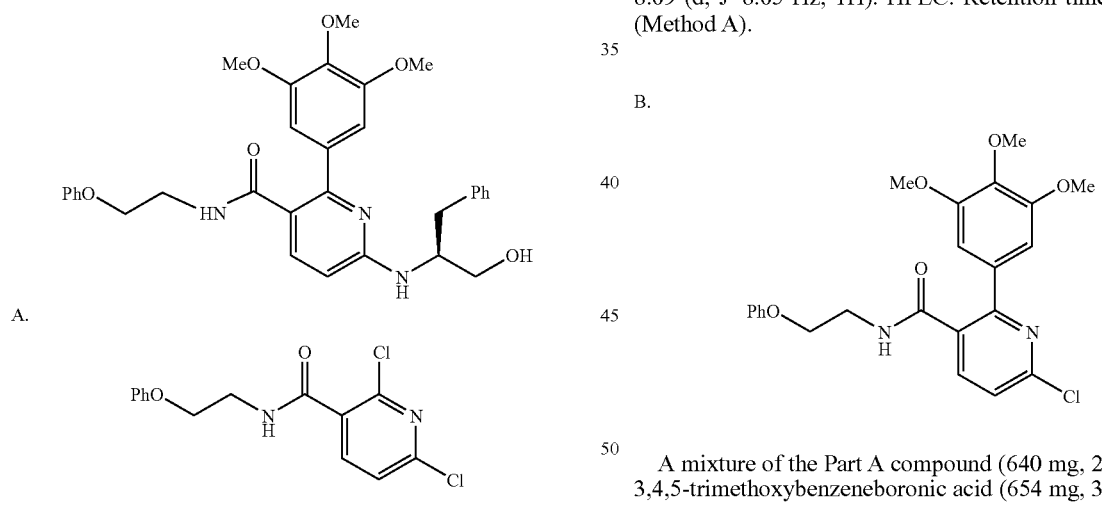

A.

To a suspension of 2,6-dichloronicotinic acid (960 mg, 5 mmol) in toluene (9 mL) was added SOCl$_2$ (547 mL, 7.5 mmol) and 2 drops of DMF. The mixture was heated at 90° C. for 2 h, then cooled to room temperature. The solvent was removed in vacuo and the residual yellow oil was dried under high vacuum overnight. The residue was dissolved in anhydrous THF (20 mL) and cooled to −78° C. Triethylamine (2.1 mL, 15 mmol) and 2-phenoxyethylamine (653 µL, 5 mmol) were added, and the reaction was stirred for 1.5 h, then quenched by pouring into a mixture of saturated NaHCO$_3$ and CH$_2$Cl$_2$. The aqueous layer was extracted with CH$_2$Cl$_2$. The organic extracts were combined and dried (MgSO$_4$), then concentrated to give a yellow oil, which was purified by flash chromatography on silica gel eluting with 35% EtOAc/hexane to give the amide as a white solid (1.78 g, 82%).

MS (ES+) m/z (M+H)$^+$=311.16. $^1$H NMR (400 MHz, CDCl$_3$): δ 3.87-3.91 (m, 2H), 4.17 (t, J=5.21 Hz, 2H), 6.90-7.04 (m, 4H), 7.26-7.32 (m, 2H), 7.36 (d, J=8.05 Hz, 1H), 8.09 (d, J=8.05 Hz, 1H). HPLC: Retention time=2.91 min (Method A).

B.

A mixture of the Part A compound (640 mg, 2.05 mmol), 3,4,5-trimethoxybenzeneboronic acid (654 mg, 3.09 mmol), K$_2$CO$_3$ (853 mg, 6.18 mmol), and POPd$_2$ (42 mg, 0.062 mmol) in THF (5 mL) in a sealed tube was heated at 80° C. overnight and the orange mixture turned to greyish suspension. The mixture was cooled to room temperature, diluted with EtOAc (50 mL), and washed with H$_2$O (30 mL). The orange organic layer was washed with brine, dried over with MgSO$_4$, then concentrated to give a light orange foam, which was purified by flash chromatography on silica gel eluting with 50% EtOAc/hexane to give the chloropyridine as a pale yellow foam (469 mg, 52%).

MS (ES+) m/z (M+H)$^+$=443.28. $^1$H NMR (400 MHz, CDCl$_3$): δ 3.61-3.65 (m, 2H), 3.81 (s, 3H), 3.84 (s, 6H), 3.88 (t, J=5.36 Hz, 2H), 5.92 (t, J=5.40 Hz, 1H), 6.73 (d, J=7.52 Hz, 1H), 6.87 (s, 2H), 6.95 (t, J=7.52 Hz, 1H), 7.22-7.29 (m, 1H), 7.36 (d, J=8.08 Hz, 1H), 7.97 (d, J=8.6 Hz, 1H). HPLC: Retention time=3.10 min (Method A).

C.

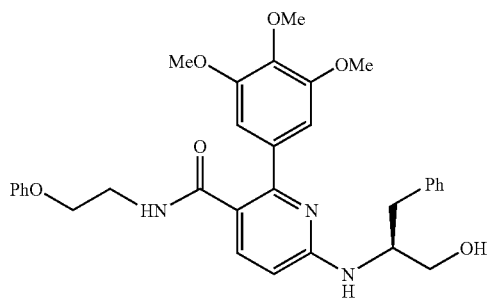

A mixture of the Part B compound (150 mg, 0.339 mmol) and (S)-2-amino-3-phenyl-propan-1-ol (513 mg, 3.39 mmol) was heated at 150° C. for 48 h, then cooled to room temperature. The crude product was purified by flash chromatography on silica gel eluting with 80% EtOAc/Hex followed by preparative HPLC (YMC S5 ODS 20×100 mm column, gradient elution 30-100% B/A over 15 min (solvent A=10% MeOH/H$_2$O containing 0.1% TFA, solvent B=90% MeOH/H$_2$O containing 0.1% TFA), flow rate 20 mL/min, UV detection at 220 nm). The product fractions were combined and concentrated in vacuo, and the residue was treated with EtOAc/NaHCO$_3$ The organic layer was washed with brine, dried and concentrated to give the title compound a white foam (85 mg, 45%).

MS (ES+) m/z (M+H)$^+$=558.49. $^1$H NMR (400 MHz, CDCl$_3$): δ 2.92 (d, J=6.72 Hz, 2H), 3.56-3.73 (m, 3H), 3.81 (s, 6H), 3.84 (s, 3H), 4.10 (b, 2H), 5.04-5.05 (m, 1H), 5.81 (brs, 1H), 6.33 (d, J=8.5 Hz, 1H), 6.73 (d, J=7.8 Hz, 2H), 6.93 (t, J=7.00 Hz, 1H), 6.79 (s, 2H), 7.20-7.28 (m, 7H), 7.79 (d, J=8.52 Hz, 1H). HPLC: Retention time=2.85 min (Method A).

Example 73

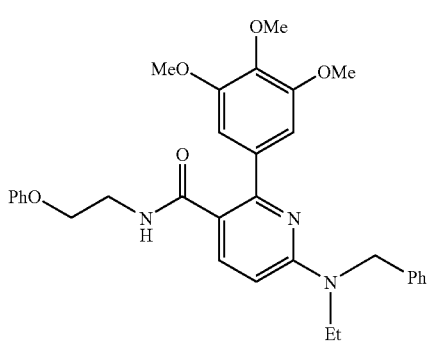

According to the procedure for the preparation of the Example 72 compound, reaction of the Example 72 Part B compound (150 mg, 0.339 mmol) and benzylethylamine (458 mg, 3.39 mmol) provided the title compound as a light brownish foam (28 mg, 15%). Two phenolic byproducts (A1 and A2) were also isolated from the reaction mixture and identified.

MS (ES+) m/z (M+H)$^+$=542.40. $^1$H NMR (400 MHz, CDCl$_3$): δ 1.23 (t, J=6.85 Hz, 3H), 3.59-3.64 (m, 4H), 3.76 (s, 6H), 3.80 (s, 3H), 4.88 (s, 2H), 5.77 (b, 1H), 6.48 (d, J=8.72 Hz, 1H), 6.74 (d, J=7.87 Hz, 2H), 6.81 (s, 2H), 6.92 (t, J=7.35 Hz, 1H), 7.25-7.30 (m, 7H), 7.84 (d, J=8.72 Hz, 1H). HPLC: Retention time=3.92 min (Method A).

A1

A2

Compound A1:

MS (ES+) m/z (M+H)$^+$=528.36. $^1$H NMR (400 MHz, CDCl$_3$): δ 1.24 (t, J=7.04 Hz, 3H), 3.58-3.69 (m, 4H), 3.76 (s, 6H), 3.81-3.84 (m, 2H), 4.84 (s, 2H), 5.86 (br s, 1H), 6.55 (d, J=8.96 Hz, 1H), 6.71 (d, J=7.84 Hz, 2H), 6.75 (s, 2H), 6.94 (m, 1H), 7.22-7.32 (m, 7H), 7.92 (d, J=8.96 Hz, 1H). HPLC: Retention time=3.62 min (Method A).

Compound A2:

MS (ES+) m/z (M+H)$^+$=528.37. $^1$H NMR (400 MHz, CDCl$_3$): δ 1.26 (t, J=7.04 Hz, 3H), 3.58-3.62 (m, 2H), 3.73-3.74 (m, 5H), 3.81 (s, 3H), 3.84-3.86 (m, 2H), 4.85 (s, 2H), 6.13 (br s, 1H), 6.61-6.62 (m, 1H), 6.66 (d, J=9.16 Hz, 1H), 6.75 (d, J=7.52 Hz, 3H), 6.94 (m, 1H), 7.21-7.35 (m, 7H), 8.00 (d, J=9.16 Hz, 1H). HPLC: Retention time=3.72 min (Method A).

Example 74

A.

-continued

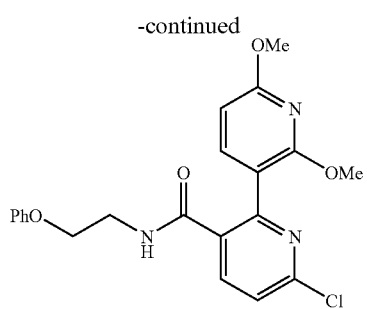

Argon was bubbled through a mixture of the Example 72 Part A compound (290 mg, 0.932 mmol), 2,6-dimethoxypyridine-3-boronic acid (170 mg, 0.932 mmol), and 0.4M aqueous $Na_2CO_3$ (4.66 mL, 1.864 mmol) in a sealed tube for several minutes. The catalyst $Pd(PPh_3)_4$ (54 mg, 0.047 mmol) was added and the sealed tube was heated at 90° C. for 16 h, and allowed to cool to room temperature. The mixture was diluted with $H_2O$ (10 mL) and extracted with EtOAc (25 mL). The extract was washed with brine, dried over $MgSO_4$, and concentrated to give a residue, which was purified by flash chromatography on silica gel eluting with 30% EtOAc/hexane to give an oil, which was further purified by preparative HPLC (YMC S5 ODS 20×100 mm column, gradient elution 40-100% B/A over 18 min (solvent A=10% $MeOH/H_2O$ containing 0.1% TFA, solvent B=90% $MeOH/H_2O$ containing 0.1% TFA), flow rate 20 mL/min, UV detection at 220 nm). The product fractions were combined and MeOH was removed in vacuo. The residue was treated with EtOAc/$NaHCO_3$. The organic layer was washed with brine, dried and concentrated to give the chloropyridine as a white foam (50 mg, 13%).

MS (ES+) m/z $(M+H)^+$=414.26. $^1$H NMR (400 MHz, $CDCl_3$): δ 3.65-3.69 (m, 2H), 3.71 (s, 3H), 3.84 (s, 3H), 3.88 (t, J=4.84 Hz, 2H), 6.26 (t, J=5.36 Hz, 1H), 6.36 (d, J=8.08 Hz, 1H), 6.72-6.74 (m, 2H), 6.97 (t, J=7.00 Hz, 1H), 7.24-7.31 (m, 3H), 7.81 (d, J=8.08 Hz, 1H), 8.00 (d, J=8.08 Hz, 1H). HPLC: Retention time=3.49 min (Method A).

B.

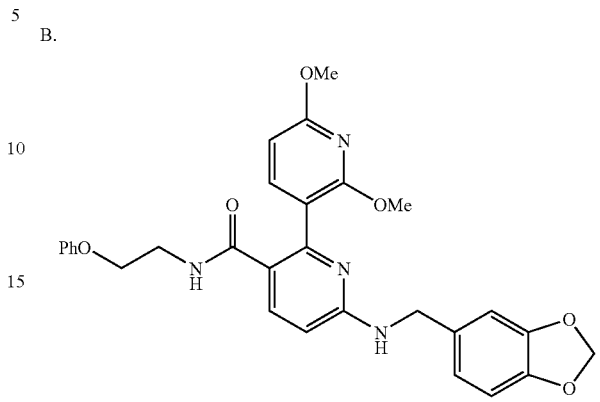

A mixture of the Part A compound (52 mg, 0.125 mmol) and 3,4-methylenedioxybenzylamine (190 mg, 1.26 mmol) was heated at 140° C. overnight. The resulting mixture was purified by flash chromatography on silica gel eluting with 70% EtOAc/hexane to give the title compound as a light brownish foam (49 mg, 74%).

MS (ES+) m/z $(M+H)^+$=529.33. $^1$H NMR (400 MHz, $CDCl_3$): δ 3.61-3.65 (m, 2H), 3.73 (s, 3H), 3.82 (t, J=4.84 Hz, 2H), 3.89 (s, 3H), 3.98 (s, 1H), 4.49 (s, 2H), 5.96 (s, 2H), 6.07 (t, J=5.45 Hz, 1H), 6.33 (d, J=8.28 Hz, 1H), 6.67-6.70 (m, 3H), 6.79-6.80 (m, 3H), 6.98 (t, J=7.36 Hz, 1H), 7.25-7.29 (m, 2H), 7.56 (d, J=8.28 Hz, 1H), 8.10 (d, J=9.33 Hz, 1H). HPLC: Retention time=2.94 min (Method A).

Examples 75 to 83

Examples 75 to 83 set out in Table 3 were prepared according to the general procedures described in Examples 72-74.

TABLE 3

![General structure: PhO-CH2CH2-NH-C(=O)-pyridine(Ar at 2-position, Y at 6-position)]

| Example No. | Ar | Y | [M + H]⁺ | HPLC R$_t$ (min) [Method] |
|---|---|---|---|---|
| 75 | 6-OMe, 2-OMe pyridin-3-yl | -NH-CH₂-(3-chlorophenyl) | 529.3 | 2.95 [A] |
| 76 | 6-OMe, 2-OMe pyridin-3-yl | -N(Et)-CH₂-phenyl | 519.3 | 3.28 [A] |

TABLE 3-continued
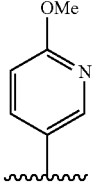
| Example No. | Ar | Y | [M + H]+ | HPLC R$_t$ (min) [Method] |
|---|---|---|---|---|
| 77 | 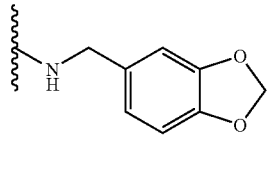 | 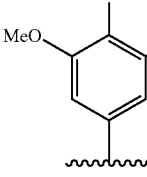 | 499.3 | 3.16 [A] |
| 78 | 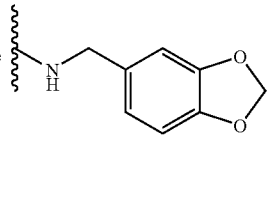 | 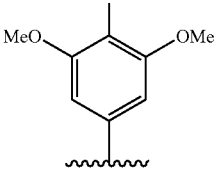 | 558.4 | 2.94 [A] |
| 79 | 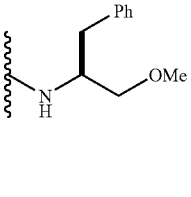 | 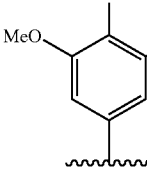 | 572.2 | 3.23 [A] |
| 80 | 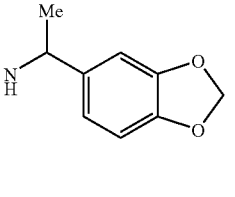 | 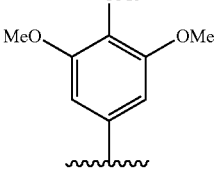 | 572.1 | 3.15 [A] |
| 81 | 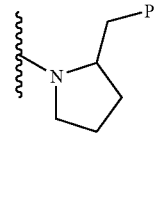 | 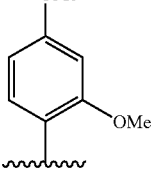 | 568.4 | 3.61 [A] |
| 82 | 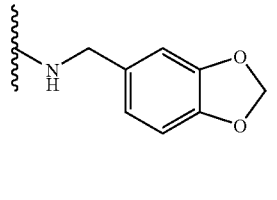 | | 528.3 | 2.74 [A] |

TABLE 3-continued

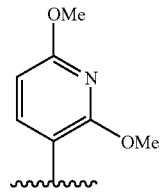

| Example No. | Ar | Y | [M + H]+ | HPLC R$_t$ (min) [Method] |
|---|---|---|---|---|
| 83 | OMe (pyridine with two OMe) | (CH-CH2OH with NH, CH2Ph side chain) | 529.2 | 2.96 [C] |

Example 84

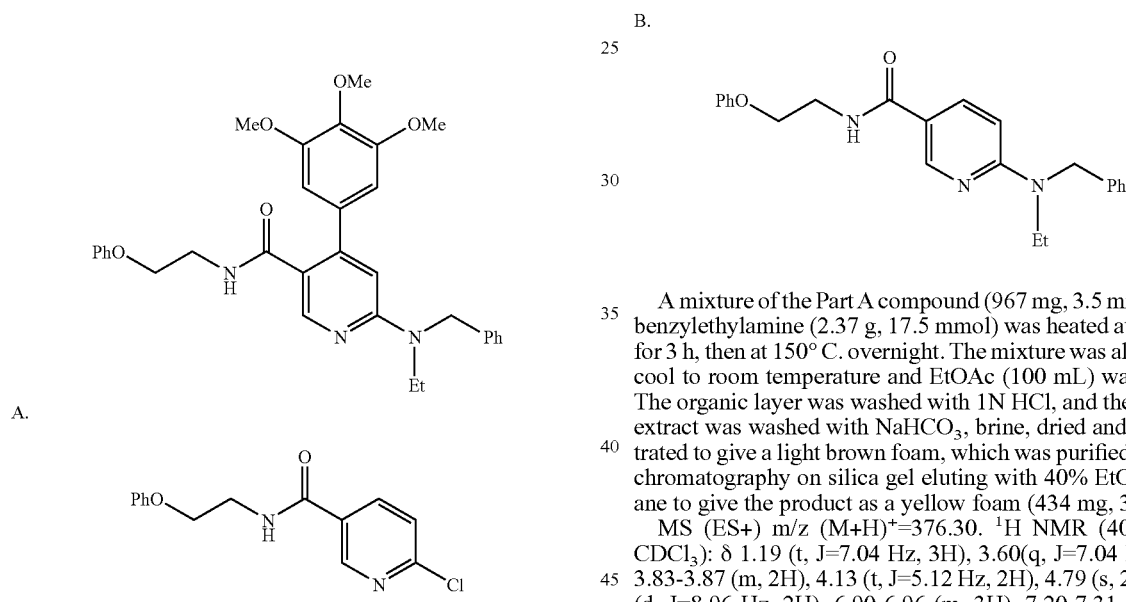

A.

A suspension of 6-chloronicotinic acid (3.94 g, 25 mmol) and SOCl$_2$ (0.74 mL, 37.5 mmol) in toluene (45 mL) was heated at reflux for 4 h, then cooled to room temperature. The solvent was removed in vacuo and the residue was dried in vacuo overnight to form a light brown solid. To this solid was added THF (100 mL) and the mixture was cooled to −78° C. Triethylamine (10.5 mL, 75 mmol) and 2-phenoxyethylamine (3.27 mL, 25 mmol) were then added. The mixture was stirred at −78° C. for 1 h, after which the reaction mixture was poured into saturated NaHCO$_3$ and extracted with EtOAc. The organinc extract was washed with brine, dried and concentrated to give a light brown solid, which was recrystallized from hexane/CH$_2$Cl$_2$ to provide the amide as a white solid (6.3 g, 91%).

$^1$H NMR (400 MHz, CDCl$_3$): δ 3.88-3.40 (m, 2H), 4.17 (t, J=5.28 Hz, 2H), 6.60 (br s, 1H), 6.91 (t, J=7.92 Hz, 2H), 6.99 (d, J=7.48 Hz, 1H), 7.28-7.32 (m, 2H), 7.41 (d, J=8.32 Hz, 1H), 8.07 (dd, J=8.32, 2.20 Hz, 1H), 8.76 (d, J=2.2 Hz, 1H). HPLC: Retention time=3.00 min (Method A).

B.

A mixture of the Part A compound (967 mg, 3.5 mmol) and benzylethylamine (2.37 g, 17.5 mmol) was heated at 100° C. for 3 h, then at 150° C. overnight. The mixture was allowed to cool to room temperature and EtOAc (100 mL) was added. The organic layer was washed with 1N HCl, and the organic extract was washed with NaHCO$_3$, brine, dried and concentrated to give a light brown foam, which was purified by flash chromatography on silica gel eluting with 40% EtOAc/hexane to give the product as a yellow foam (434 mg, 33%).

MS (ES+) m/z (M+H)$^+$=376.30. $^1$H NMR (400 MHz, CDCl$_3$): δ 1.19 (t, J=7.04 Hz, 3H), 3.60(q, J=7.04 Hz, 2H), 3.83-3.87 (m, 2H), 4.13 (t, J=5.12 Hz, 2H), 4.79 (s, 2H), 6.46 (d, J=8.96 Hz, 2H), 6.90-6.96 (m, 3H), 7.20-7.31 (m, 6H), 7.84 (dd, J=8.96, 2.24 Hz, 1H), 8.59 (d, J=2.24 Hz, 1H). HPLC: Retention time=3.10 min (Method A).

C.

To a solution of the Part B compound (380 mg, 1.01 mmol) and TMEDA (457 μL, 3.03 mmol) in THF (5.6 mL) was slowly added n-BuLi (1.6M in hexane, 1.89 mL, 3.03 mL) at −78° C. The reaction mixture was kept at −40° C. overnight then recooled to −78° C. A solution of iodine (346 mg, 1.36 mmol) in THF (0.56 mL) was added dropwise. The mixture was allowed to warm to 0° C. for 10 min, Na$_2$S$_2$O$_3$.5H$_2$O (843 mg, 3.39 mmol) in H₂O (2.33 mL) was added dropwise, followed by ether (20 mL) and H₂O (20 mL). The aqueous layer was extracted with CH₂Cl₂ (2×10 mL). The organic extracts were combined, dried over MgSO₄ and concentrated to give an orange foam, which was purified by flash chromatography on silica gel eluting with 0-50% EtOAc/hexane to give the iodide as a yellow foam (67.8 mg, 13%).

MS (ES+) m/z (M+H)⁺=502.21. ¹H NMR (400 MHz, CDCl₃): δ 1.15 (t, J=7.04 Hz, 3H), 3.50(q, J=7.04 Hz, 2H), 3.80-3.85 (m, 2H), 4.13 (t, J=5.28 Hz, 2H), 4.73 (s, 2H), 6.46 (t, J=5.28 Hz, 1H), 6.86-6.97 (m, 4H), 7.16-7.32 (m, 6H), 8.22 (s, 1H). HPLC: Retention time=3.76 min (Method A).

D.

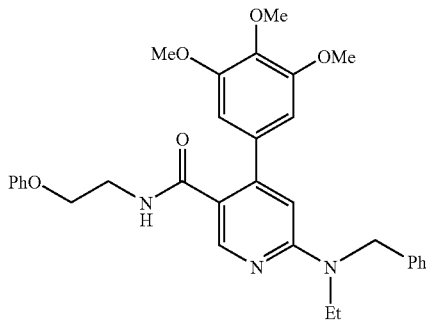

To a mixture of the Part C compound (67.8 mg, 0.135 mmol) and 3,4,5-trimethoxybenzeneboronic acid (28.7 mg, 0.135 mmol) was added 0.4 M aqueous Na₂CO₃ solution (337 μL) and CH₃CN (377 μL). Argon was bubbled through the reaction mixture for two minutes and Pd(PPh₃)₄ (8 mg) was added. The mixture was heated at 90° C. for 4 h, then cooled to room temperature. EtOAc was added, and the mixture was dried over MgSO₄ then concentrated in vacuo. The crude product was purified by flash chromatography on silica gel eluting with 70% EtOAc/hexane to give the title compound as an off-white foam (52 mg, 71%).

MS (ES+) m/z (M+H)⁺=542.29. ¹H NMR (400 MHz, CDCl₃): δ 1.20 (t, J=7.04 Hz, 3H), 3.58-3.65 (m, 4H), 3.75 (s, 6H), 3.80 (s, 3H), 3.86 (t, J=5.04 Hz, 2H), 4.80 (s, 2H), 5.86 (b, 1H), 6.27 (s, 1H), 6.49 (s, 2H), 6.73-6.76 (m, 2H), 6.94 (t, J=7.36 Hz, 1H), 7.22-7.30 (m, 7H), 8.63 (s, 1H). HPLC: Retention time=3.41 min (Method A).

Example 85

A.

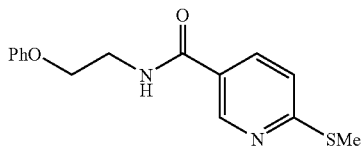

To a solution of the Example 84 Part A compound (2.2 g, 7.97 mmol) in DMF (5 mL) was added NaSMe (4.5 mL, 15% in H₂O, 10.4 mmol). The reaction mixture was stirred at room temperature overnight before it was diluted with EtOAc (100 mL), washed with H₂O (3×100 mL), dried over MgSO₄, and concentrated to give the thioether as a white solid (1.98 g, 86%).

MS (ES+) m/z (M+H)⁺=289.19. ¹H NMR (400 MHz, CDCl₃): δ 2.59 (s, 3H), 3.89(dd, J=5.4, 10.2 Hz, 2H), 4.16 (t, J=5.1 Hz, 2H), 6.56 (brs, 1H), 6.92 (d, J=8.1 Hz, 1H), 6.98 (t, J=7.3 Hz, 1H), 7.24 (t, J=8.6 Hz, 1H), 7.28-7.32 (m, 2H), 7.89 (dd, J=2.7, 8.6 Hz, 1H), 8.81 (d, J=1.6 Hz, 1H). HPLC: Retention time=3.11 min (Method A).

B.

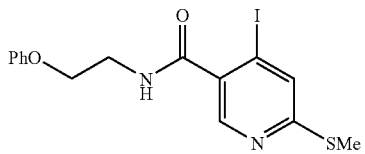

To a solution of the Part A compound (1.24 g, 4.3 mmol) and TMEDA (1.4 mL, 9.5 mmol) in THF (5.6 mL) at −78° C. was added n-BuLi (1.6 M in hexane, 5.9 mL, 9.5 mmol) dropwise via a syringe pump over 1 h. A solution of iodine (5.5 g, 21.5 mmol) in THF (50 mL) was added dropwise over 2 h. The reaction was maintained at −78° C. for additional 1 h before being quenched with saturated aqueous NH₄Cl. An aqueous Na₂S₂O₃ solution was then added and the mixture was extracted with EtOAc (2×50 mL). The organic layer was dried over MgSO₄, concentrated and purified by flash chromatography on silica gel eluting with a gradient of 0% to 50% EtOAc/hexane to provide the iodide as a white solid (488 mg, 27%).

MS (ES+) m/z (M+H)⁺=415.08. ¹H NMR (400 MHz, CDCl₃): δ 2.41 (s, 3H), 3.50-3.84 (m, 4H), 6.76 (d, J=8.1 Hz, 2H), 6.84 (s, 1H), 6.94 (t, J=7.3 Hz, 1H), 7.24 (t, J=8.1 Hz, 2H), 7.77 (t, J=5.7 Hz, 1H), 8.37 (s, 1H). HPLC: Retention time=3.16 min (Method A).

C.

To a mixture of the Part B compound (488 mg, 1.18 mmol) and 2,4-dimethoxy-3-pyridineboronic acid (316 mg, 1.72 mmol) in a sealed tube was added 0.4M aqueous Na₂CO₃ solution (6 mL) and CH₃CN (6 mL). Argon was bubbled through the reaction mixture for several minutes, after which Pd(PPh₃)₄ (108 mg, 0.09 mmol) was added. The reaction mixture was heated at 120° C. for 16 h, cooled to room temperature, and partitioned between EtOAc and H₂O. The organic layer was dried over MgSO₄, concentrated and purified by flash chromatography on silica gel, eluting with a gradient of 0% to 50% EtOAc/hexane to give the product as a white gum (241 mg, 48%).

MS (ES+) m/z (M+H)⁺=426.27. ¹H NMR (400 MHz, CDCl₃): δ 2.58 (s, 3H), 3.67 (dd, J=5.3, 10.4 Hz, 2H), 3.75 (s, 3H), 3.83 (s, 3H), 3.89 (t, J=4.9 Hz, 2H), 6.21 (t, J=5.3 Hz, 1H), 6.31 (d, J=8.1 Hz, H), 6.77 (d, J=7.8 Hz, 2H), 6.96 (t, J=7.3 Hz, H), 7.04 (s, 1H), 7.26 (t, J=8.1 Hz, 2H), 7.46 (d, J=8.1 Hz, 1H), 8.72 (s, 1H). HPLC: Retention time=3.61 min (Method C).

D.

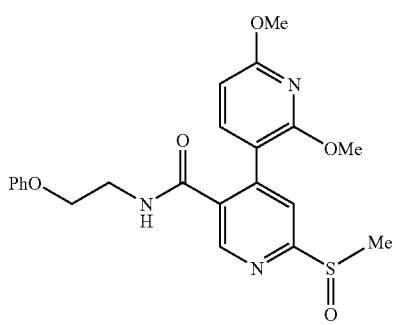

To a solution of the Part C compound (241 mg, 0.57 mmol) in CH₂Cl₂ (5 mL) at 0° C. was added 2-benzenesulfonyl-3-phenyl-oxaziridine (157 mg, 0.6 mmol). The reaction mixture was warmed to room temperature and stirred overnight. The solvent was removed and the crude residue was purified by flash chromatography on silica gel, eluting with a gradient of 0% to 100% EtOAc/hexane to give the sulfoxide as a white solid (258 mg, 100%).

MS (ES+) m/z (M+H)⁺=442.23. ¹H NMR (400 MHz, CDCl₃): δ 2.81 (s, 3H), 3.70 (dd, J=5.3, 10.5 Hz, 2H), 3.76 (s, 3H), 3.82 (s, 3H), 3.93-3.97 (m, 2H), 6.25 (d, J=8.1 Hz, H), 6.80 (d, J=7.9 Hz, 2H), 6.96 (t, J=7.4 Hz, 1H), 7.03 (t, J=5.4 Hz, H), 7.25-7.30 (m, 2H), 7.46 (d, J=8.1 Hz, 1H), 7.76 (s, 1H), 8.75 (s, 1H). HPLC: Retention time=3.03 min (Method C).

E.

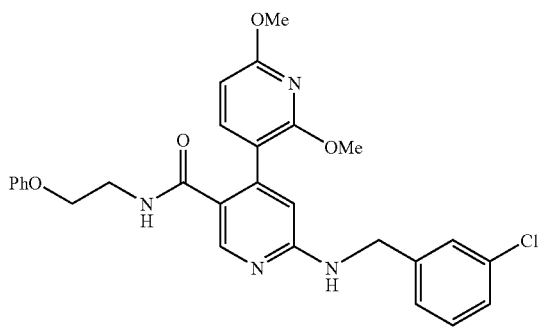

A mixture of the Part D compound (9.4 mg, 0.02 mmol) and m-chlorobenzylamine (0.3 mL, 2.47 mmol) was heated at 140° C. for 16 h, then cooled to room temperature. The crude product was purified by preparative HPLC (YMC S5 ODS 20×100 mm column, gradient elution 30-100% B/A over 15 min (solvent A=10% MeOH/H₂O containing 0.1% TFA, solvent B=90% MeOH/H₂O containing 0.1% TFA), flow rate 20 mL/min, UV detection at 220 nm) to give the title compound as a white solid (8.0 mg, 50%).

MS (ES+) m/z (M+H)⁺=519.10. ¹H NMR (400 MHz, CDCl₃): δ 3.68 (dd, J=5.3, 10.3 Hz, 2H), 3.76 (s, 3H), 3.77 (s, 3H), 3.93 (t, J=5.0 Hz, 2H), 4.54 (d, J=3.2 Hz, 2H), 6.21 (brs, 1H), 6.32 (d, J=8.2 Hz, 1H), 6.49 (s, 1H), 6.76 (d, J=7.9 Hz, 2H), 6.98 (t, J=7.3 Hz, 1H), 7.19-7.32 (m, 6H), 8.26 (s, 1H). HPLC: Retention time=3.28 min (Method A).

Examples 86 to 90

Examples 86 to 90 set out in Table 4 were prepared according to the general procedures described in Example 84 and Example 85.

TABLE 4

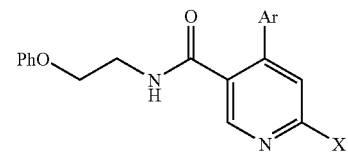

| Example No. | Ar | X | [M + H]⁺ | HPLC Rₜ (min) [Method] |
|---|---|---|---|---|
| 86 | 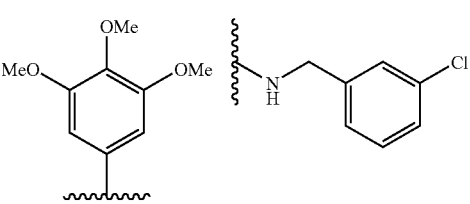 | | 548.3 | 3.12 [C] |

TABLE 4-continued

| Example No. | Ar | X | [M + H]⁺ | HPLC R$_t$ (min) [Method] |
|---|---|---|---|---|
| 87 | 3,4,5-trimethoxyphenyl | NH-CH2-benzodioxole | 558.3 | 2.81 [C] |
| 88 | 2,6-dimethoxypyridin-3-yl | NH-CH2-benzodioxole | 529.3 | 3.07 [C] |
| 89 | 3,4,5-trimethoxyphenyl | NH-CH(CH2Ph)-CH2OH | 538.4 | 2.82 [C] |
| 90 | 2,6-dimethoxypyridin-3-yl | NH-CH(CH2Ph)-CH2OH | 529.1 | 3.10 [C] |

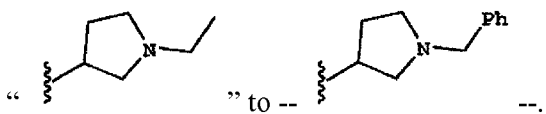

What is claimed is:

1. A compound having the structure

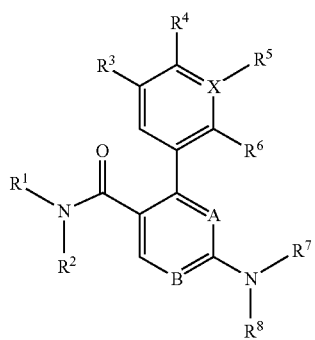

wherein
X is C;
A and B are each N;
R$^1$ is Ar-L-;
R$^2$ is hydrogen or alkyl;
Ar is aryl or heteroaryl;
L is a linking group containing 1 to 6 atoms in a linear chain, which may be all carbons or may have one or two hetero atoms in the chain selected from N, O, and S, and may be substituted with one, two, three or four substituents;
R$^3$ and R$^5$ are each independently alkyl, cycloalkyl, alkenyl, alkynyl, alkoxy, hydroxy, haloalkyl, haloalkoxy, nitro, cyano, trifluoromethyl, trifluoromethoxy, amino, alkylamino, thiol, alkylthio, alkylsulfinyl, or alkylsulfonyl;
R$^4$ is alkyl, cycloalkyl, alkenyl, alkynyl, alkoxy, hydroxy, haloalkyl, haloalkoxy, nitro, cyano, trifluoromethyl, trifluoromethoxy, amino, alkylamino, thiol, alkylthio, alkylsulfinyl, or alkylsulfonyl;
R$^6$ is selected from hydrogen, alkyl, cycloalkyl, alkenyl, alkynyl, alkoxy, hydroxy, halo, haloalkyl, haloalkoxy, nitro, cyano, trifluoromethyl, trifluoromethoxy, amino, alkylamino, thiol, alkylthio, alkylsulfinyl, or alkylsulfonyl;

$R^7$ is alkyl, cycloalkyl, cycloalkylalkyl, cycloheteroalkyl, cycloheteroalkylalkyl, arylalkyl, heteroarylalkyl, arylaminoalkyl, or arylthioalkyl;

$R^8$ is hydrogen or alkyl;

provided that $R^1$ and $R^2$ cannot be phenylmethylene or phenylethylene;

or a pharmaceutically acceptable salt thereof, or all stereoisomers thereof;

wherein the term "alkyl" alone or as part of another group may be optionally substituted with one, two, three or four substituents (which may be the same or different) commonly attached to such chains, selected from the group consisting of halo, $CF_3$, alkyl, alkoxy, aryl, aryloxy, aryl(aryl) or diaryl, arylalkyl, arylalkyloxy, alkenyl, alkynyl, cycloalkyl, cycloalkenyl, cycloalkylalkyl, cycloalkylalkyloxy, optionally substituted amino, hydroxy, hydroxyalkyl, acyl, oxo, alkanoyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, alkoxycarbonyl, alkylaminocarbonyl, nitro, cyano, thiol, haloalkyl, trihaloalkyl, alkylthio, and carboxyl;

the term "Ar" or "aryl" alone or as part of another group
a) may be optionally fused to an aryl, cycloalkyl, heteroaryl or cycloheteroalkyl ring; and
b) may be optionally substituted through available carbon atoms with one to four substituents, selected from the group consisting of hydrogen, halo, haloalkyl, alkyl, alkoxy, haloalkoxy, alkenyl, trifluoromethyl, trifluoromethoxy, alkynyl, cycloalkylalkyl, cycloheteroalkyl, cycloheteroalkylalkyl, aryl, heteroaryl, arylalkyl, heteroarylalkyl, aryloxy, aryloxyalkyl, alkoxyalkyl, arylalkoxy, alkoxycarbonyl, aryloxycarbonyl, arylalkoxycarbonyl, arylalkenyl, heteroarylalkenyl, heteroarylheteroaryl, heteroaryloxy, heteroarylalkoxy, heteroaryloxyalkyl, aminocarbonylalkyl, aminocarbonylaryl, arylthio, arylalkylthio, heteroarylalkylthio, arylazo, hydroxy, nitro, cyano, carboxyl, carboxylalkoxy, alkoxycarbonylalkoxy, amino, and substituted amino, wherein the amino includes 1 or 2 substituents which are selected from the group consisting of alkyl, aryl, thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, alkylsulfonyl, arylsulfonyl, heteroarylsulfonyl, cycloheteroalkylsulfonyl, alkylsulfinyl, arylsulfinyl, arylsulfinylalkyl, arylsulfonylamino, arylsulfonaminocarbonyl and/or any of the alkyl substituents set out above;

the term "heteroaryl" alone or as part of another group
a) may be optionally fused to an aryl, cycloalkyl, heteroaryl or cycloheteroalkyl ring; and
b) may be optionally substituted by one to four substituents which can be any of the "alkyl" substituents or "aryl" substituents as defined above;

the term "cycloheteroalkyl" alone or as part of another group
a) may be optionally fused to a cycloalkyl, aryl, heteroaryl or cycloheteroalkyl ring; and
b) may be optionally substituted with 1 to 4 substituents selected from the group consisting of alkyl, halo, oxo and any of the substituents for "alkyl" or "aryl" as defined above;

the term "cycloalkyl" alone or as part of another group
a) may be optionally fused to an aryl, cycloalkyl, heteroaryl or cycloheteroalkyl ring; and
b) may be optionally substituted with one to four substituents selected from the group consisting of halogen, alkyl, alkoxy, hydroxyl, aryl, aryloxy, arylalkyl, cycloalkyl, alkylamido, alkanoylamino, oxo, acyl, arylcarbonylamino, amino, nitro, cyano, thiol and/or alkylthio and/or any of the substituents for "alkyl" as defined above;

the term "alkenyl" alone or as part of another group may be optionally substituted with 1 to 4 substituents selected from the group consisting of halogen, haloalkyl, alkyl, alkoxy, alkenyl, alkynyl, aryl, arylalkyl, cycloalkyl, amino, hydroxyl, heteroaryl, cycloheteroalkyl, alkanoylamino, alkylamido, arylcarbonylamino, nitro, cyano, thiol, alkylthio and/or any of the substituents for alkyl as defined above; and the term "alkynyl" alone or as part of another group may be optionally substituted with 1 to 4 substituents selected from the group consisting of halogen, haloalkyl, alkyl, alkoxy, alkenyl, alkynyl, aryl, arylalkyl, cycloalkyl, amino, heteroaryl, cycloheteroalkyl, hydroxyl, alkanoylamino, alkylamido, arylcarbonylamino, nitro, cyano, thiol, and/or alkylthio, and/or any of the substituents for "alkyl" as defined above.

2. The compound as defined in claim 1 wherein $R^1$ is phenyl-O-alkylene; and $R^2$ is hydrogen.

3. The compound as defined in claim 1 wherein $R^3$ and $R^5$ are each independently alkyl, alkoxy, hydroxy, haloalkyl, haloalkoxy, trifluoromethyl, or trifluoromethoxy;

$R^4$ is alkyl, alkoxy, hydroxy, haloalkyl, haloalkoxy, trifluoromethyl, or trifluoromethoxy;

$R^7$ is alkyl, cycloalkylalkyl, arylalkyl, or heteroarylalkyl;

$R^8$ is hydrogen or alkyl.

4. The compound as defined in claim 1 wherein L may be substituted with one, two, three or four substituents which may be the same or different and are independently selected from alkyl, alkoxy, aryl, cycloalkyl, haloalkyl, hydroxy, oxo (=O), arylalkyl, heteroaryl or cycloheteroaryl.

5. The compound as defined in claim 1 wherein $R^1$ is Ar-L-;

$R^2$ is hydrogen;

Ar is phenyl;

L is alkylene or —O-alkylene-;

$R^3$ and $R^5$ are each independently alkyl, alkoxy, hydroxy, haloalkyl, haloalkoxy, trifluoromethyl, or trifluoromethoxy;

$R^4$ is alkyl, alkoxy, hydroxy, haloalkyl, haloalkoxy, trifluoromethyl, or trifluoromethoxy;

$R^7$ is alkyl, cycloalkylalkyl, arylalkyl, or heteroarylalkyl;

$R^8$ is hydrogen or alkyl.

6. The compound as defined in claim 1 wherein $R^1$ is $C_6H_5OCH_2CH_2$, 4-$ClC_6H_4$—$CH_2CH(CH_3)$—, or 4-$C_2H_5C_6H_4CH_2CH_2$;

$R^2$ is H, $R^3$ is $CH_3O$, $R^4$ $CF_3$, or $CH_3O$, $R^5$ is $CH_3O$, $R^6$ is H, Cl, or $CH_3O$, $R^7$ is benzyl, or 2-Cl-benzyl, or

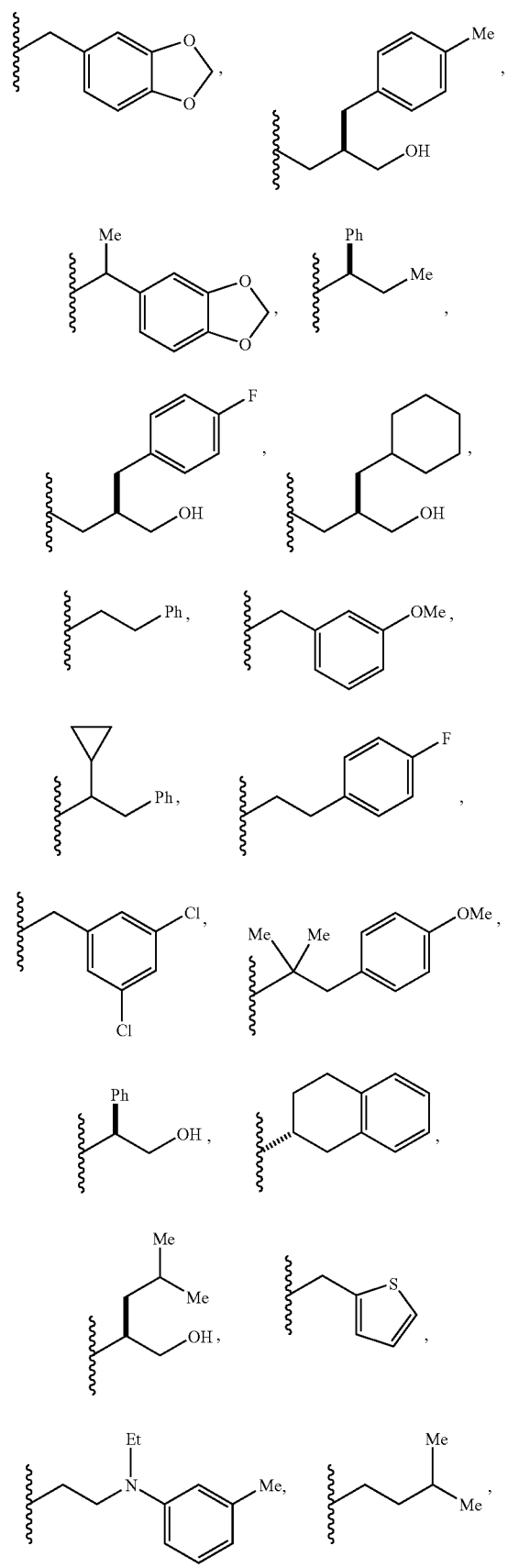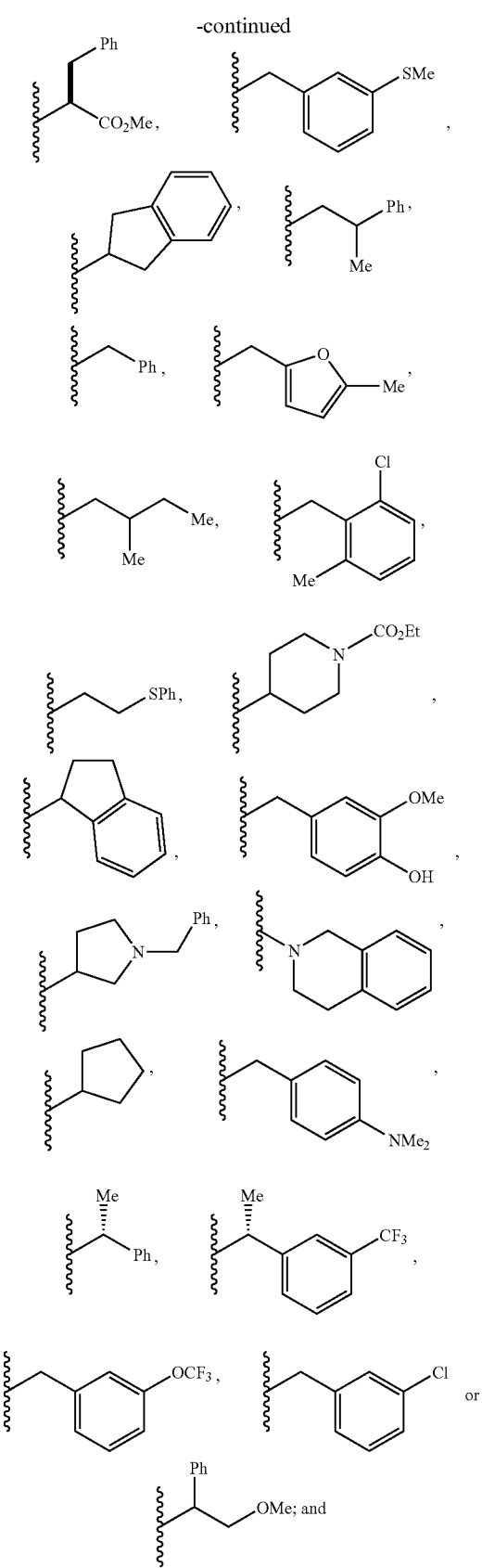
$R^8$ is H, $CH_3$, $C_2H_5$, or $HOC_2H_4$.

7. The compound as defined in claim 1 having the structure

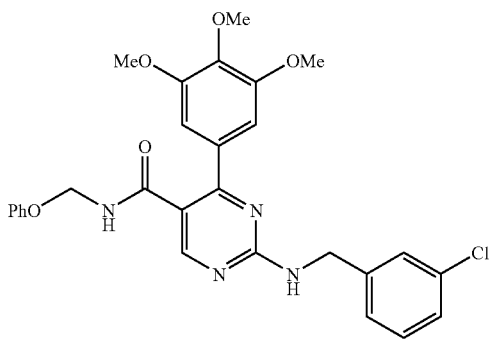

or a pharmaceutically acceptable salt thereof.

8. A pharmaceutical composition comprising a compound as defined in claim 1 and a pharmaceutically acceptable carrier therefor.

9. A compound having the structure

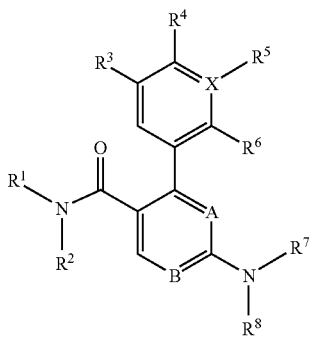

wherein
X is N;
A and B are each N;
$R^1$ is Ar-L-;
$R^2$ is hydrogen or alkyl;
or $R^1$ and $R^2$ can be joined together to form a 4- to 7-membered cycloheteroalkyl ring;
Ar is aryl or heteroaryl;
L is a linking group containing 1 to 6 atoms in a linear chain, which may be all carbons or may have one or two hetero atoms in the chain selected from N, O, and S, and may be substituted with one, two, three or four substituents;
$R^3$ and $R^6$ are each independently hydrogen, alkyl, cycloalkyl, alkenyl, alkynyl, alkoxy, hydroxy, halo, haloalkyl, haloalkoxy, nitro, cyano, trifluoromethyl, trifluoromethoxy, amino, alkylamino, thiol, alkylthio, alkylsulfinyl, or alkylsulfonyl;
$R^4$ is alkyl, cycloalkyl, alkenyl, alkynyl, alkoxy, hydroxy, halo, haloalkyl, haloalkoxy, nitro, cyano, trifluoromethyl, trifluoromethoxy, amino, alkylamino, thiol, alkylthio, alkylsulfinyl, or alkylsulfonyl;
$R^7$ is alkyl, cycloalkyl, cycloalkylalkyl, cycloheteroalkyl, cycloheteroalkylalkyl, arylalkyl, heteroarylalkyl, arylaminoalkyl, or arylthioalkyl;
$R^8$ is hydrogen or alkyl;
or $R^7$ and $R^8$ can be joined together to form a 4- to 7-membered cycloheteroalkyl ring;

or a pharmaceutically acceptable salt thereof, or all stereoisomers thereof;
wherein the term "alkyl" alone or as part of another group may be optionally substituted with one, two, three or four substituents (which may be the same or different) commonly attached to such chains, selected from the group consisting of halo, $CF_3$, alkyl, alkoxy, aryl, aryloxy, aryl(aryl) or diaryl, arylalkyl, arylalkyloxy, alkenyl, alkynyl, cycloalkyl, cycloalkenyl, cycloalkylalkyl, cycloalkylalkyloxy, optionally substituted amino, hydroxy, hydroxyalkyl, acyl, oxo, alkanoyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, alkoxycarbonyl, alkylaminocarbonyl, nitro, cyano, thiol, haloalkyl, trihaloalkyl, alkylthio, and carboxyl;
the term "Ar" or "aryl" alone or as part of another group
a) may be optionally fused to an aryl, cycloalkyl, heteroaryl or cycloheteroalkyl ring; and
b) may be optionally substituted through available carbon atoms with one to four substituents, selected from the group consisting of hydrogen, halo, haloalkyl, alkyl, alkoxy, haloalkoxy, alkenyl, trifluoromethyl, trifluoromethoxy, alkynyl, cycloalkylalkyl, cycloheteroalkyl, cycloheteroalkylalkyl, aryl, heteroaryl, arylalkyl, heteroarylalkyl, aryloxy, aryloxyalkyl, alkoxyalkyl, arylalkoxy, alkoxycarbonyl, aryloxycarbonyl, arylalkoxycarbonyl, arylalkenyl, heteroarylalkenyl, heteroarylheteroaryl, heteroaryloxy, heteroarylalkoxy, heteroaryloxyalkyl, aminocarbonylalkyl, aminocarbonylaryl, arylthio, arylalkylthio, heteroarylalkylthio, arylazo, hydroxy, nitro, cyano, carboxyl, carboxylalkoxy, alkoxycarbonylalkoxy, amino, and substituted amino, wherein the amino includes 1 or 2 substituents which are selected from the group consisting of alkyl, aryl, thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, alkylsulfonyl, arylsulfonyl, heteroarylsulfonyl, cycloheteroalkylsulfonyl, alkylsulfinyl, arylsulfinyl, arylsulfinylalkyl, arylsulfonylamino, arylsulfonaminocarbonyl and/or any of the alkyl substituents set out above;
the term "heteroaryl" alone or as part of another group
a) may be optionally fused to an aryl, cycloalkyl, heteroaryl or cycloheteroalkyl ring; and
b) may be optionally substituted by one to four substituents which can be any of the "alkyl" substituents or "aryl" substituents as defined above;
the term "cycloheteroalkyl" alone or as part of another group
a) may be optionally fused to a cycloalkyl, aryl, heteroaryl or cycloheteroalkyl ring; and
b) may be optionally substituted with 1 to 4 substituents selected from the group consisting of alkyl, halo, oxo and any of the substituents for "alkyl" or "aryl" as defined above;
the term "cycloalkyl" alone or as part of another group
c) may be optionally fused to an aryl, cycloalkyl, heteroaryl or cycloheteroalkyl ring; and
d) may be optionally substituted with one to four substituents selected from the group consisting of halogen, alkyl, alkoxy, hydroxyl, aryl, aryloxy, arylalkyl, cycloalkyl, alkylamido, alkanoylamino, oxo, acyl, arylcarbonylamino, amino, nitro, cyano, thiol and/or alkylthio and/or any of the substituents for "alkyl" as defined above;

the term "alkenyl" alone or as part of another group may be optionally substituted with 1 to 4 substituents selected from the group consisting of halogen, haloalkyl, alkyl, alkoxy, alkenyl, alkynyl, aryl, arylalkyl, cycloalkyl, amino, hydroxyl, heteroaryl, cycloheteroalkyl, alkanoylamino, alkylamido, arylcarbonylamino, nitro, cyano, thiol, alkylthio and/or any of the substituents for alkyl as defined above; and the term "alkynyl" alone or as part of another group may be optionally substituted with 1 to 4 substituents selected from the group consisting of halogen, haloalkyl, alkyl, alkoxy, alkenyl, alkynyl, aryl, arylalkyl, cycloalkyl, amino, heteroaryl, cycloheteroalkyl, hydroxyl, alkanoylamino, alkylamido, arylcarbonylamino, nitro, cyano, thiol, and/or alkylthio, and/or any of the substituents for "alkyl" as defined above.

10. The compound as defined in claim 9 wherein $R^1$ is phenyl-alkylene or phenyl-O-alkylene; and
$R^2$ is hydrogen or $R^1$ and $R^2$ are joined together to form an aryl-substituted piperidinyl ring or an aryl-substituted benzofused piperidinyl.

11. The compound as defined in claim 9 wherein
$R^3$ and $R^6$ are each independently hydrogen, alkyl, alkoxy, hydroxy, halo, haloalkyl, haloalkoxy, trifluoromethyl, or trifluoromethoxy;
$R^4$ is alkyl, alkoxy, hydroxy, halo, haloalkyl, haloalkoxy, trifluoromethyl, or trifluoromethoxy;
$R^7$ is alkyl, cycloalkylalkyl, arylalkyl, or heteroarylalkyl;
$R^8$ is hydrogen or alkyl;
or $R^7$ and $R^8$ can be joined together to form a pyrrolidinyl or piperidinyl ring.

12. The compound as defined in claim 9 wherein L may be substituted with one, two, three or four substituents which may be the same or different and are independently selected from alkyl, alkoxy, aryl, cycloalkyl, haloalkyl, hydroxy, oxo (=O), arylalkyl, heteroaryl or cycloheteroaryl.

13. The compound as defined in claim 9 wherein
$R^1$ is Ar-L-;
$R^2$ is hydrogen;
or $R^1$ and $R^2$ can be joined together to form an aryl-substituted piperidinyl ring or an aryl-substituted benzofused piperidinyl ring;
Ar is phenyl;
L is alkylene or —O-alkylene-;
$R^3$ and $R^6$ are each independently hydrogen, alkyl, alkoxy, hydroxy, halo, haloalkyl, haloalkoxy, trifluoromethyl, or trifluoromethoxy;
$R^4$ is alkyl, alkoxy, hydroxy, halo, haloalkyl, haloalkoxy, trifluoromethyl, or trifluoromethoxy;
$R^7$ is alkyl, cycloalkylalkyl, arylalkyl, or heteroarylalkyl;
$R^8$ is hydrogen or alkyl;
or $R^7$ and $R^8$ can be joined together to form a pyrrolidinyl or piperidinyl ring.

14. The compound as defined in claim 9 wherein
$R^1$ is $C_6H_5OCH_2CH_2$, $4\text{-}ClC_6H_4\text{—}CH_2CH(CH_3)\text{—}$, or $4\text{-}C_2H_5C_6H_4CH_2CH_2$,
$R^2$ is H,
or $R^1$ and $R^2$ are taken together with the N to which they are attached to form

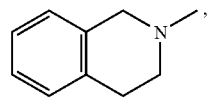

$R^3$ is H, or $CH_3O$,
$R^4$ $CF_3$, or $CH_3O$,
$R^6$ is H, Cl, or $CH_3O$,
$R^7$ is benzyl, or 2-Cl-benzyl, or

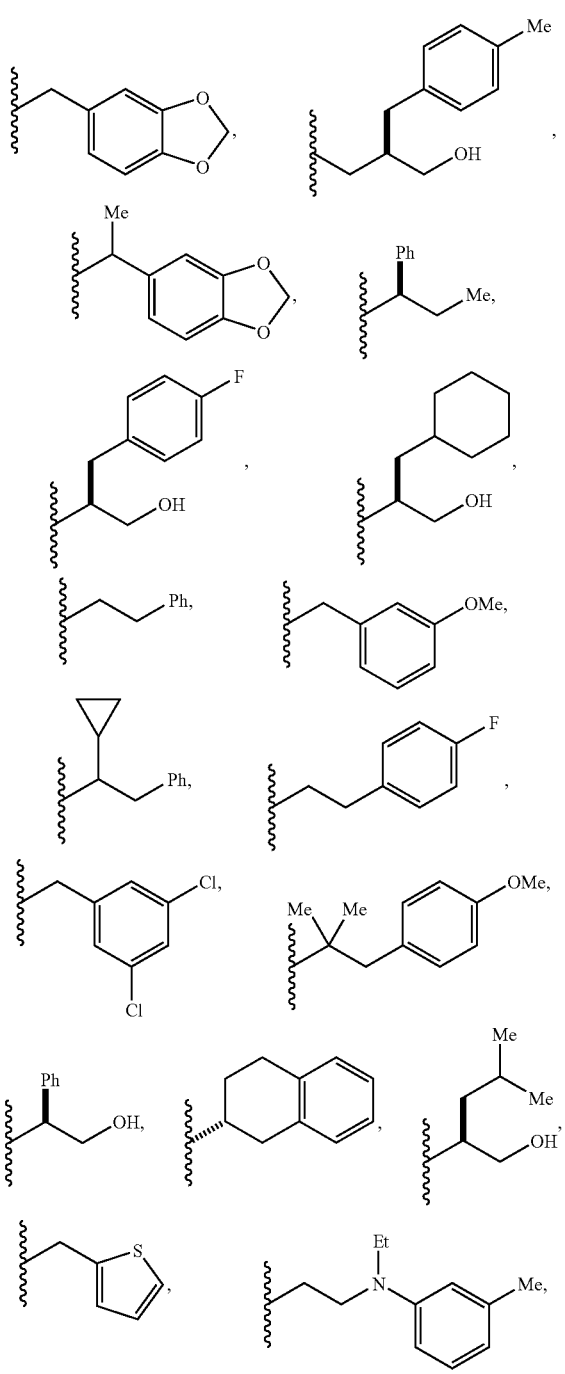

-continued

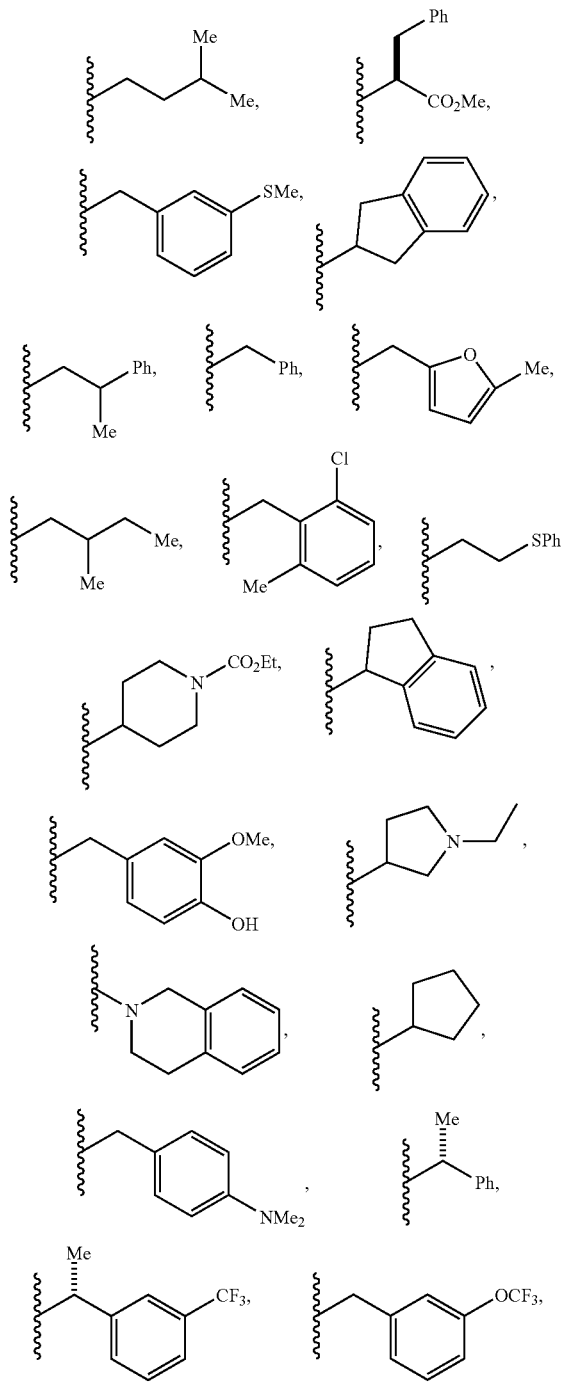

-continued

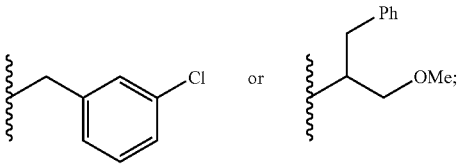

$R^8$ is H, $CH_3$, $C_2H_5$, or $HOC_2H_4$;

or $R^7$ and $R^8$ are taken together with the N to which they are attached to form the following rings:

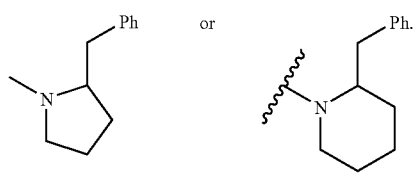

15. The compound as defined in claim 9 having the structure

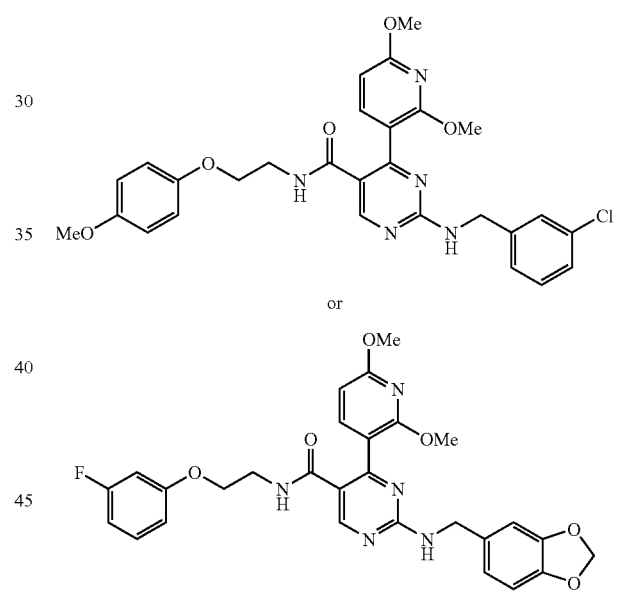

or a pharmaceutically acceptable salt thereof.

16. A pharmaceutical composition comprising a compound as defined in claim 9 and a pharmaceutically acceptable carrier therefor.

* * * * *

UNITED STATES PATENT AND TRADEMARK OFFICE
CERTIFICATE OF CORRECTION

PATENT NO. : 7,459,460 B2  Page 1 of 2
APPLICATION NO. : 10/854484
DATED : December 2, 2008
INVENTOR(S) : Wu Yang et al.

It is certified that error appears in the above-identified patent and that said Letters Patent is hereby corrected as shown below:

On the Title Page:

Item (56), References Cited, under FOREIGN PATENT DOCUMENTS,
  Change "WO 00/43279" to -- WO 00/73279 --.

In the Claims:

Claim 6:

Column 76, line 63, after "$R^{4}$", insert -- is --.
  Column 77, lines 18 to 24, change

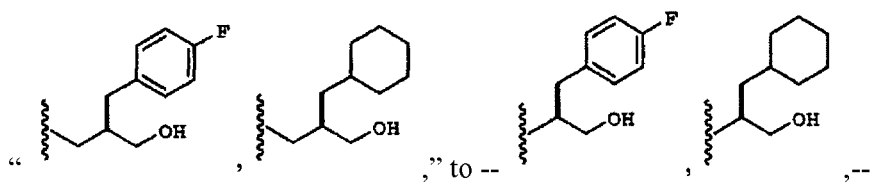

Signed and Sealed this
Twenty-ninth Day of March, 2011

David J. Kappos
*Director of the United States Patent and Trademark Office*

CERTIFICATE OF CORRECTION (continued)
U.S. Pat. No. 7,459,460 B2

Page 2 of 2

In the Claims:

Claim 7:
    Column 79, lines 4 to 15, change

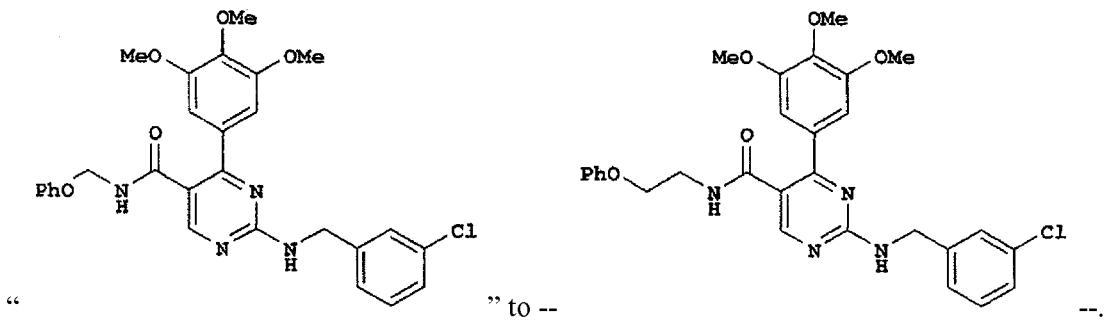

Claim 9:
    Column 79, lines 25 to 37, change

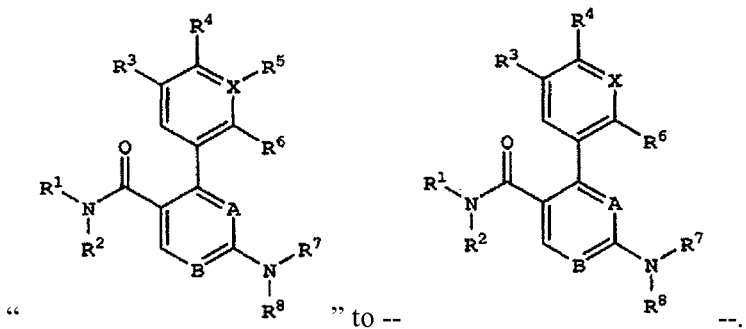

Claim 14:
    Column 82, line 10, after "$R^4$", insert -- is --.

Column 83, lines 32 to 37, change